US008764686B2

(12) United States Patent
Nishihara et al.

(10) Patent No.: US 8,764,686 B2
(45) Date of Patent: Jul. 1, 2014

(54) FETAL MOVEMENT INFORMATION PROCESSING DEVICE AND FETAL MOVEMENT INFORMATION PROCESSING METHOD

(75) Inventors: Kyoko Nishihara, Fuchu (JP); Nobuyuki Ozawa, Kawasaki (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 1049 days.

(21) Appl. No.: 12/309,936

(22) PCT Filed: Aug. 3, 2007

(86) PCT No.: PCT/JP2007/065301
§ 371 (c)(1),
(2), (4) Date: Feb. 3, 2009

(87) PCT Pub. No.: WO2008/016151
PCT Pub. Date: Feb. 7, 2008

(65) Prior Publication Data
US 2009/0270767 A1    Oct. 29, 2009

(30) Foreign Application Priority Data

Aug. 4, 2006  (JP) ................................. 2006-213767

(51) Int. Cl.
*A61B 5/117*  (2006.01)
*A61B 5/103*  (2006.01)

(52) U.S. Cl.
USPC ...................................................... 600/595

(58) Field of Classification Search
USPC .......................... 600/587, 595, 300, 301, 588
See application file for complete search history.

(56) References Cited

FOREIGN PATENT DOCUMENTS

| JP | S63-501196 | 5/1988 |
|----|------------|--------|
| JP | S63-192421 | 8/1988 |
| JP | H5-141 | 1/1993 |
| JP | H10-511015 | 10/1998 |
| JP | H11-89832 | 4/1999 |
| JP | 2003-52690 | 2/2003 |
| JP | 2004-337332 | 12/2004 |
| JP | 2005-304996 | 11/2005 |
| WO | WO 2006/082977 | 8/2006 |

OTHER PUBLICATIONS

Eugenius S.B.C. Ang, Jr. et al., "Prenatal exposure to ultrasound waves inpacts neuronal migration in mice", PNAS, Aug. 22, 2006, pp. 12903-12901, vol. 103 No. 34.

*Primary Examiner* — Brian Szmal
(74) *Attorney, Agent, or Firm* — DLA Piper LLP (US)

(57) ABSTRACT

A fetal movement information processing device and method for accurately grasping and predicting the healthy development state of a fetus, namely, the well-being state of the fetus by adequately detecting and recording information on the fetal movement of a pregnant woman. The fetal movement information processing device comprises detected information storage means (20) for storing fetal movement detection signal detected by a fetal movement sensor (11) and detection day information associated with the fetal movement detection signal, pregnancy number-of-elapsed-days calculating means (38) for calculating the number of elapsed days from the fetal movement detection signals, fetal movement amount measuring means (54) for measuring the fetal movement amount per unit time from fetal movement signals read out from the detected information storage means, and displaying/outputting means (60) for displaying the fetal movement amounts acquired by the fetal movement amount measuring means and arranged in order of week of pregnancy.

15 Claims, 15 Drawing Sheets

FETAL MOVEMENT TYPE DETERMINATION

LARGE AND SLOW FETAL MOVEMENT: L>SL2 AND T>ST
LARGE AND FAST FETAL MOVEMENT: L>SL2 AND T<=ST
SMALL AND SLOW FETAL MOVEMENT: SL1<L<SL2 AND T>ST
SMALL AND FAST FETAL MOVEMENT: SL1<L<SL2 AND T<=ST
(SL1, 2 : SLICE LEVEL 1, 2    ST : SLICE TIME)

33 YEARS OLD, 36 WEEKS OF GESTATION

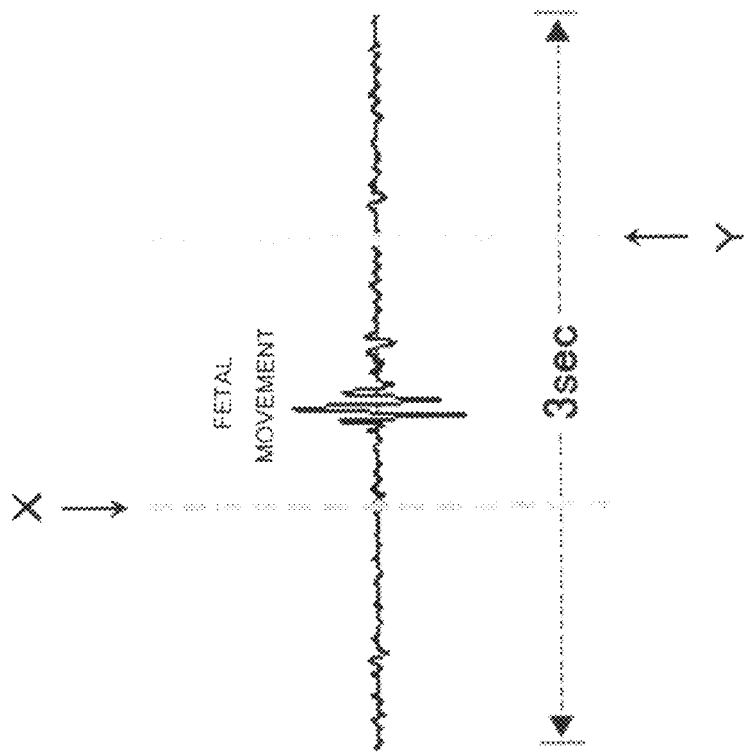
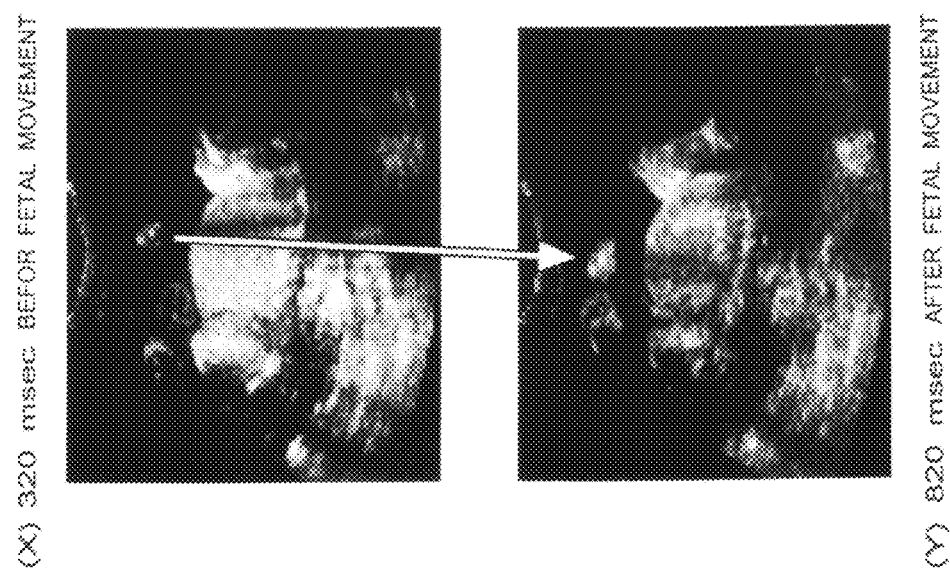
FIG. 15

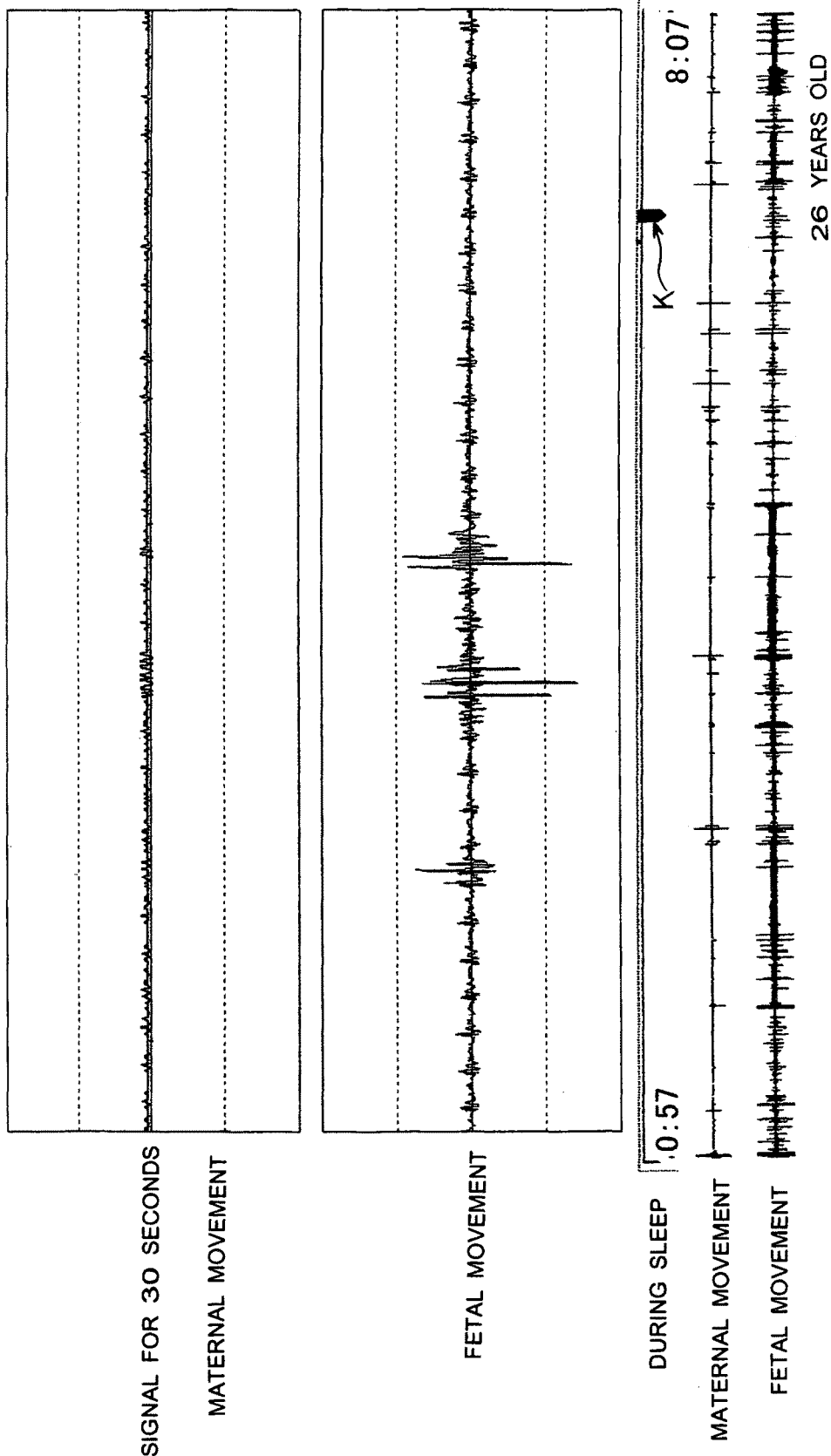

FETAL MOVEMENT INFORMATION PROCESSING DEVICE AND FETAL MOVEMENT INFORMATION PROCESSING METHOD

TECHNICAL FIELD

The present invention relates to a fetal movement information processing device and a fetal movement information processing method. The present invention relates to a device and a method for detecting and recording information about fetal movements of a pregnant woman and enabling accurate grasp or prediction of a healthy growth state of the fetus, namely, a well-being state of the fetus. It becomes possible for a healthy pregnant woman to do domestic management of a fetus with safety and peace of mind by using a device and a method according to the present invention under the supervision of a doctor or a midwife. Furthermore, it also becomes possible to find an abnormal condition of a fetus in a uterus early. The present invention also relates to a fetal movement information processing device and a fetal movement information processing method which are able to transfer fetus information to a doctor appropriately and promptly with respect to a pregnant woman having a risk factor and thereby exhibit a screening function and perform medical care for a pregnant woman in a hospital adequately and efficiently.

BACKGROUND ART

Up to now, fetal movement frequency detecting methods and detecting devices are known which detect the number of fetal movements perceived by a pregnant woman in a fixed period of time in order to grasp whether a fetus is growing smoothly in a uterus.

As such fetal movement frequency detecting methods and devices, various kinds of methods and devices have been proposed and implemented which are configured so that a pregnant woman pushes a button when feeling a fetal movement or so that a fetal movement sensor for detecting fetal movements is attached on a pregnant woman's abdomen in order to determine whether there is a fetal movement on the basis of an output signal from the fetal movement sensor.

For example, a technique disclosed in Japanese Unexamined Patent Publication No. 11-89832 (Patent Document 1), detects fetal movements using a thin-film piezoelectric sensor, and determines that the fetus is healthy if a predetermined number 10 or more of fetal movements are detected within a fixed period of time (two hours). A technique is disclosed about a fetal movement measuring instrument which determines that the fetus is in a dangerous condition if the number of fetal movements in a fixed period of time (8 hours) is less than a predetermined number 10.

However, there are differences among fetuses and among the numbers of fetal movements caused when a fetus moves actively, rests, and so on by time period, so that it is difficult to determine whether the fetus is growing healthy or not from the number of fetal movements. In addition, there are various types of fetal movement including those occurring for a few minutes at intervals of two or three seconds such as "hiccups" and those occurring singly such as "kicks" and "rolls". When such types of fetal movement are taken into consideration, it is extremely difficult to predict or determine well-being of a fetus only by detecting a fetal movement frequency as described above.

Furthermore, no movement of a fetus in a fixed period of time cannot necessarily decide that the fetus is in a dangerous condition. For example, the tendency has been confirmed that a change in fetal movement of a healthy pregnant woman gradually becomes remarkable and the number of occurrences of it increases from 20 weeks of gestation. In addition, the tendency has been confirmed that at a time of delivery a fetus in a uterus moves downward and thereby fetal movements cannot be detected appropriately by a normal fetal movement sensor resulting in a small change in fetal movement and a reduced frequency of it.

In addition, high sensitivity employed for detecting fetal movements in a uterus by signals from a pregnant woman's abdomen catches a signal from the woman by her movement such as respiration and heart beats to count as one component of fetal movement, thereby shows a number beyond actual fetal movements, resulting in a risk of missing that the fetus has a reduction in fetal movement.

Furthermore, in Japanese Unexamined Patent Publication No. 10-511015 (Patent Document 2), a fetus monitoring device is disclosed which is configured so as to receive an electric signal representing an activity of a fetus from a sensor which is a pressure or acceleration detector using a piezoelectric film and is attached to a pregnant woman's abdomen, compare the electric signal with predetermined signal series by a comparator, and produce an output representing activity of the fetus. A device and a method for monitoring a fetus configured like this are assumed to serve to provide objective data of growth of a fetus to an obstetrician or the like to detect a disease or abnormality of the fetus.

The proposed fetus monitoring device detects, with a sensor, small movements caused by heart beats, breathing movements, and movements of the body of a fetus, converts these movements to electric signals, and identifies the movements by the frequency components of them. Furthermore, it has also been proposed that two or more sensors are used to clearly distinguish signals indicative of fetus movements and thereby signals caused by various physiological movements of a pregnant woman such as physical movements, respiration, and heart beats of the pregnant woman are simultaneously recorded.

In this proposal, the sensitivity of the sensor is likely to be raised to record movements of a fetus, heart beats, and breathing movements of the fetus, and for this reason, respiration and heart beats of the pregnant woman are detected as signals, so that signals of the pregnant woman are mixed with signals from the fetus resulting a difficult distinction between both. According to FIG. 7, the problem that the heart rate of a fetus becomes 300 times or more for one minute occurs. In other words, in this case, signals including those of the pregnant woman are shown and movements of the fetus are not recorded accurately. Moreover, it is shown that respiration movements of the pregnant woman are picked up very easily when a piezoelectric film is used as the sensor.

Furthermore, in this proposal, how to deal with individual differences among fetuses and fetal movements including, as described above, those occurring two or more times at a constant cycle such as "hiccups", those occurring singly such as "kicks" and "rolls", and the like is not disclosed at all. It is difficult to determine concrete fetal movements from analysis of frequency components, and is not sufficient to predict or determine well-being of a fetus.

Furthermore, it is assumed that the predetermined comparator includes the heart rate, breathing movements, and physical movements of a fetus, but growing processes of the fetus by weeks from the conception are not almost considered, so that it is impossible to compare these signals. Thus, the proposed device is not able to determine that a fetus is in a dangerous condition. In other words, as described above, at least the following tendencies are observed in fetal movements of a healthy pregnant woman. (1) The tendency has been confirmed that a change in fetal movement gradually becomes remarkable and the number of occurrences of fetal movement increases from the 20 weeks of gestation. (2) The tendency has been confirmed that at a time of delivery a fetus in a uterus moves downward and thereby fetal movements cannot be detected appropriately by a normal fetal movement sensor resulting in a small change in fetal movement and a reduced frequency of it. Processing by a simple comparator based on the same criteria of determination without consideration of these tendencies of fetal movement in different periods of time means that information processing related to fetal movements corresponding to stages of growth of a fetus is performed, and its problem awareness is not shown at all. Thus, it is difficult to appropriately predict or determine well-being of a fetus by the proposed device or method.

Patent Document 1: Japanese Unexamined Patent Publication (Kokai-Koho) No. 11-89832

Patent Document 2: Japanese Unexamined Patent Publication (Kohyo-Koho) No. 10-511015

Non-patent Document 1: Eugenius S. B. C. Ang, Jr. et al., "Prenatal exposure to ultrasound waves impacts neuronal migration in mice", PNAS, Aug. 22, 2006, vol. 103, No. 34, 12903-12910

DISCLOSURE OF THE INVENTION

Problems to be Solved by the Invention

The Patent Document 1 describes that the components of a pregnant woman's respiration is subtracted from the output of a fetal movement sensor by inverted filtration based on a multidimensional autoregressive (AR) model. However, the AR model is effective on a regular signal, but is not able to sufficiently address movements such as the pregnant woman's respiration which vary to a large degree depending on the physical condition and/or mental state of the pregnant woman or whether the pregnant woman is sleeping or awake, especially large fluctuations of respiration during arousal/REM sleep, and may therefore make an erroneous determination due to the pregnant woman's respiration.

At present, a delivery monitoring device/ultrasound tomography device is useful for an ultrasound examination as clinical use, and has reduced the perinatal mortality rate. In spite of this, there is no method of preventing unexplained death of a fetus in a uterus, and the appearance ratio of cerebral palsy has not reduced also at the present time when delivery monitoring devices have been spread. It is considered that there is a large possibility that this is due to some causes during fetal life, and it is difficult for present ultrasound examination methods to pursue the causes because of short-time measurement. Long-term monitoring is necessary for obtaining a healthy growth state, namely a well-being state, of a fetus.

However, the influence of long-term use of ultrasound is unknown, and it is not much recommended for health of a fetus. There is a report of research which is a report of an animal experiment saying that application of ultrasound to a pregnant mouse for 30 minutes or more causes a change in development of nerve cells of the brain of a fetus of the mouse (see non-patent document 1). Thus, a fetus movement is a good index to determine well-being of a fetus, so that it is considered that long-time monitoring by a passive sensor picking up a fetus movement is most suitable.

For this reason, the inventor et al used a biological phenomenon recording/reproducing device (Medilog 9200 made by Oxford Ltd., England) using an electrical capacitance acceleration detection type sensor developed as a fetal movement sensor by the inventor for a healthy primipara (32 years old) to measure fetal movements within a required period of time while sleeping for each of pregnancy weeks at home. As a result, the followings were found. In FIG. 11, characteristic parts of pregnancy weeks are extracted for the order of one hour of sleeping time overnight.

(1) 21 Weeks of Gestation

A pregnant woman came to feel a fetal movement before and after the 20 weeks, and at this time, an attachment position of a fetal movement sensor was decided and measurement and record of fetus movement were started. The measurement signal in this period had included large breathing signals of the pregnant woman which interfered with fetal movement signals. In addition, the measurement signal had included heart beats of the pregnant woman (see FIG. 11($a$)).

(2) 24 Weeks of Gestation

From the result of 21 weeks, the pregnant woman was able to decide an attachment position of the fetal movement sensor to a position where no respiration movement was included in the measurement signal and to a position where fetal movements were active and was able to record fetal movements (see FIG. 11($b$)).

(3) 28 Weeks of Gestation

From the experience of the 21 weeks and the 24 weeks, it came to be possible to make a record of fetal movement with stability. It is said that a pregnant woman feels many fetal movements from this time to around 32 weeks, and it was confirmed that fetal movements were recorded frequently at this time (see FIG. 11($c$)).

(4) 32 Weeks of Gestation

As with the 28 weeks, even if respiration movements and heart beats of the pregnant woman were included in a measurement signal, fetal movements were able to be recorded relatively clearly (see FIG. 11($d$)).

(5) 36 Weeks of Gestation

In this week also, fetal movements were recorded appropriately. In addition, a time period when an occurrence rate of fetal movements was high and a time period when an occurrence rate of fetal movement was low were observed, which can not be represented in this one-hour figure (see FIG. 11($e$)). This is estimated to be the prototype of a rest/activity rhythm, namely, the prototype of a sleep/arousal rhythm, of a fetus.

From these results, as described above, the tendency is confirmed that a change in fetal movement gradually becomes remarkable and the number of occurrences of it increases from the 20 weeks of gestation, and it is clear that a change in fetal movement and the number of fetal movements tend to be small at a time of delivery. For this reason, if fetal movement measurement is performed on a regular basis, the date of delivery can also be estimated.

Furthermore, clinical confirmation was made about evaluation of fetal movement during arousal and sleep of a pregnant woman.

(A) Subjective Evaluations of Fetal Movement of Pregnant Women During Arousal 29 pregnant women in 19 to 39 weeks of gestation are laid down for one hour and half in the daytime, and a biological phenomenon recording/reproducing device (Medilog 9200 made by Oxford Ltd., England, or Polymate made by TEAC Ltd.) was used, as described above, to record fetal movements with sleep polygraphies (electroencephalograms, electromyograms, electro-oculograms, respiration, electrocardiograms, and the like) of the pregnant women. In this case, the pregnant women pushed down a button when feeling a fetal movement. As a result, the subjective evaluations of the pregnant women agreed with their fetal movement signals as shown in FIG. 12. FIG. 12 shows evaluation markers, breathing signals, an electrocardiogram, and fetal movement signals of a pregnant woman. In FIG. 12, a fetal movement was observed in two positions and it was confirmed that a fetal movement evaluation mark by awareness of the pregnant woman was recorded in two positions with the same timing. Furthermore, in this case, as shown in FIG. 13, fetal movement signals were confirmed for almost all pregnant woman's markers. As a whole, a fetal movement was able to be detected for 85% of the subjective evaluations of the pregnant women. On the other hand, examples that a pregnant woman did not push her button although a fetal movement signal was picked up were also confirmed.

(B) Micro-Arousals Induced by Fetal Movements During Sleep

A polygraphy (electroencephalograms, electromyograms, electro-oculograms, respiration, electrocardiograms, and the like) and fetal movements during sleep of a pregnant woman in late pregnancy were recorded at the same time. As a result, as shown in FIG. 14, a signal of a relatively large movement appeared in the center of a fetal movement signal, accompanied with alpha wave activity which appeared for about three seconds in brain waves of the pregnant woman. This alpha wave activity shows a micro-arousal of the pregnant woman. The brain waves of the pregnant woman before this alpha wave activity showed sleep stage 3 where she was from moderate sleep to deep sleep. It was confirmed that in this stage the fetus moved to stimulate the wall of the uterus of the pregnant woman and thereby the alpha wave activity of the pregnant woman appeared through the afferent nerve system and the thalamocortical circuit of the brain and then the pregnant woman returned to moderate sleep. In this period, there was an arousal for only three seconds, and it was confirmed that the arousal was different from a subjective evaluation during the above arousal of the pregnant woman and depending on the character trait and the concentration of attention of the pregnant woman, and was one of objectively high accuracy.

(C) Considering that simultaneous recording by an ultrasound tomography device and a device using the fetal movement sensor is necessary from the result of (A), simultaneous recording was performed with cooperation of 6 pregnant women (21 weeks to 36 weeks). In this case, recording was performed using a visual data recorder (AQ-VU made by TEAC Ltd.) capable of recording an analog signal and an image signal in synchronization with each other. FIG. 15 shows a fetal movement signal for three seconds and images of the ultrasound tomography device before and after the fetal movement. In other words, the figure shows an image (X) at 320 msec before a hand or a portion of the body of a fetus in 24 weeks of gestation moves and an image (Y) at 820 msec after the movement. At two time divisions A and B indicated with dotted lines of the fetal movement signal for three seconds, a point in time X is an image position before the fetus moved and a point in time Y is an image position when the fetus moved. It is confirmed by these images that the position of the hand of the fetus moved. In this experiment, subjective fetal movement evaluation markers of the pregnant woman was simultaneously recorded with fetal movements, but there was a case that the pregnant woman did not push the button although a fetal movement was recorded by the ultrasound tomography device and a fetal movement signal was able to be picked up. FIG. 15 shows such a case, and as the cause of it, it is considered that the pregnant woman did not notice the fetal movement, that she was not able to distinguish the distention of the abdomen from the fetal movement, that she did not push the button when noticing the fetal movement, or the like. Thus, it was confirmed clearly that information obtained by a device using the fetal movement sensor is valued accurately and objective more than a subjective fetal movement evaluation of a pregnant woman.

In addition, the influence of body movement of a pregnant woman (maternal movement) was removed to raise the accuracy of fetal movement information. In order to record body movements of a pregnant woman, a sensor which is the same as or different from a fetal movement sensor is attached to the pregnant woman, and fetal movements during maternal sleep and maternal movements were detected and recorded at the same time. As a result, it is confirmed that fetal movements appear earlier than maternal movements as shown in FIG. 2(a), and therefore it is clear that only a small number of signals are remained by removing fetal movement signals in the period of time when the maternal movements occurred, but fetal movement information which is more accurate than the fetal movement signals including the maternal movement signals can be obtained.

As a result of doing examination repeatedly based on matters confirmed by the above fetal movement measurement of a pregnant woman, the inventor has succeeded in developing a fetal movement information processing system which appropriately detects and records information about fetal movements in the uterus of a pregnant woman by performing the following fetal movement information processing, is able to accurately grasp and predict a healthy growth state of the fetus, namely, a well-being state of the fetus, enables a healthy pregnant woman to do domestic management of the fetus with safety and peace of mind under the supervision of a doctor or a midwife, makes it easy to find an abnormal condition of a fetus in a uterus early, and is able to achieve easy management in a hospital capable of transferring fetus information to a doctor appropriately and promptly with respect to a pregnant woman having a risk factor.

(1) Fetal movement signals and biological signals of a pregnant woman overnight (during maternal sleep) are recorded at the same time, the signals of the pregnant woman are removed from the fetal movement signals, and primary processing such as identification and quantitative determination of classification based on the time series variations of fetal movements, the total number of the fetal movements, and the characteristics of the fetal movements at that time is performed;

(2) As weeks of gestation advance, recording of fetal movements overnight is made two or more times every week as appropriate, and simultaneous display of fetal movement record at that time and simultaneous display of the raw data and subsequent primary processing data are made;

(3) Many pieces of data related to fetal movements are collected and standardized for each of pregnancy weeks, and the mean value and the standard deviation of the total number of fetal movements overnight, for example, are let to be able to be displayed from 20 weeks to 40 weeks of gestation; and (4) As a result of this, a system is constructed which is capable of providing, as diagnostic information, how data obtained about a pregnant woman's own fetus is positioned against standardized data.

It is therefore an object of the present invention to detect and record information about fetal movements by a fetal movement sensor and accurately grasp and predict a healthy growth state, namely, a well-being state of the fetus. Furthermore, a device and/or a method according to the present invention are used under the supervision of a doctor or a midwife in order to enable a health pregnant woman to do domestic management of a fetus with safety and peace of mind. Furthermore, it is an object of the present invention to provide a fetal movement information processing device and a fetal movement information processing method which are able to serve a screening function as a previous stage making it easy to find an abnormal condition of a fetus in a uterus early by processing fetal movement information in an appropriate manner, and are able to transfer fetus information to a doctor appropriately and promptly with respect to a pregnant woman having a risk factor, thereby serving to make management in a hospital easy and efficient.

Means for Solving the Problems

In order to achieve the above object, a fetal movement signal collecting device as claimed in claim 1 of the present invention comprises: at least one fetal movement sensor (11, 111) attached to a pregnant woman's abdomen for detecting fetal movements; an inspecting means (13, 113) inspecting whether or not the fetal movement sensor is normally operating; and a fetal movement detected information storage means (20, 120) storing a fetal movement detection signal detected by the fetal movement sensor in association with detection time information indicating times when the fetal movements are detected.

The fetal movement signal collecting device as claimed in claim 2 of the present invention comprises: a fetal movement sensor (11, 111) attached to a pregnant woman's abdomen for detecting fetal movements; a maternal movement sensor (12, 112) for detecting maternal movements; an inspecting means (13, 14, 113, 114) receiving a fetal movement signal output from the fetal movement sensor and a maternal movement signal output from the maternal movement sensor and inspecting whether or not the fetal movement sensor and the maternal movement sensor are each normally operating; and a fetal movement detected information storage means (20, 120) storing both a fetal movement detection signal detected by the fetal movement sensor and a maternal movement detection signal detected by the maternal movement sensor in association with detection time information indicating times when the both detection signals are detected.

The fetal movement signal collecting device as claimed in claim 3 of the present invention is characterized in that the fetal movement sensor is an electrical capacitance acceleration detection type sensor of a structure with a weight pasted on a movable film.

The fetal movement information processing device as claimed in claim 4 of the present invention is characterized in that said detected information storage means is set so as to continuously store fetal movement signals and maternal movement signals during maternal sleep overnight along with a set time.

The fetal movement information processing device as claimed in claim 5 of the present invention comprises: a fetal movement information processing means (40, 50, 140, 150) calculating a fetal movement amount per unit time every week of pregnancy of a pregnant woman based on a fetal movement signal from a fetal movement sensor, detection time information indicating times when fetal movements are detected, information identifying the pregnant woman, and number of pregnancy days information, and a display/output means (60) capable of arranging and displaying fetal movement amounts obtained by said fetal movement information processing means in order of pregnancy weeks.

The fetal movement information processing device as claimed in claim 6 of the present invention is characterized in that said fetal movement information processing means includes a number of pregnancy days calculating means (38, 138) receiving fetal movement detection time information and pregnancy information to calculate a number of pregnancy days; a detected information reading means (42, 144) reading out a detection signal from a fetal movement detected information storage means; a fetal movement information shaping means (44, 144) for shaping the read out detection signal to extract fetal movement signals, and a fetal movement amount measuring means (54, 154) measuring a fetal movement amount per unit time from fetal movement information shaped by said fetal movement information shaping means.

The fetal movement information processing device as claimed in claim 7 of the present invention is characterized in that said fetal movement information processing means further includes a detected information reading means (42) reading fetal movement signals by the fetal movement sensor and maternal movement signals by a maternal movement sensor, and a fetal movement information shaping means (44) establishing association between the fetal movement signals and the maternal movement signals which have been read out by the detected information reading means, removing fetal movement signals influenced by maternal movements when the output levels of the maternal movement signals stored at the same time are a fixed level or more, and outputting fetal movement signals less influenced by maternal movements.

The fetal movement information processing device as claimed in claim 8 of the present invention is characterized in that said fetal movement information processing means further includes a database constructed in advance by calculating a mean value and a standard deviation of fetal movement amounts for each of the pregnancy weeks based on fetal movement information about fetal movement amounts per unit time for each of the pregnancy weeks collected from many pregnant women in advance, and a calculating means calculating fetal movement amounts per unit time based on collected fetal movement signals, and said display/output means graphically displays fetal movement amounts obtained from fetal movement signals collected from the pregnant women along with mean values and standard values obtained from said database.

The fetal movement information processing device as claimed in claim 9 of the present invention is characterized in that said fetal movement information processing means further includes a database constructed in advance by calculating, based on fetal movement information about fetal movement amounts per unit time collected for each type of fetal movements and for each of the pregnancy weeks from many pregnant women in advance, a mean value and a standard deviation of fetal movement amounts for each type of fetal movements and for each of the pregnancy weeks, and a calculating means calculating fetal movement amounts per unit time based on collected fetal movement signals, and said display/output means graphically displays fetal movement amounts obtained from fetal movement signals collected from the pregnant women along with mean values and standard deviations obtained from said database, for each type of fetal movements.

The fetal movement information processing method as claimed in claim 10 of the present invention comprises: the step of inputting pregnancy information such as information identifying a pregnant woman and information for calculating number of pregnancy days (STEP-1, STEP-2); the step of reading and displaying fetal movement signals detected by a fetal movement sensor in association with detection time information indicating times when the fetal movements are detected (STEP-12, STEP-13); the fetal movement information processing step of calculating fetal movement amounts per unit time based on the read out fetal movement signals (STEP-25); and the step of displaying and outputting the fetal movement signals or the fetal movement amounts for each of the pregnancy weeks (STEP-30).

The fetal movement information processing method as claimed in claim 11 of the present invention includes the step of classifying the read out fetal movement signals for each type of the fetal movements (STEP-19 to STEP-24), and the step of calculating and displaying fetal movement amounts per unit time based on fetal movement information classified for each type of the fetal movements (STEP-25 to STEP-27).

The fetal movement information processing method as claimed in claim 12 of the present invention includes the step of rectifying the read out fetal movement signals and integrating them every unit time (STEP-32) and calculates fetal movement amounts per unit time based on fetal movement information including obtained integrated values.

The fetal movement information processing method as claimed in claim 13 of the present invention further comprises the step of continuously storing fetal movement signals and maternal movement signals during maternal sleep overnight along with times and displaying waveforms of these signals simultaneously with a time line (STEP-13) and the step of designating a time of said time line and enlarging and displaying the waveforms of fetal movement signals and maternal movement signals at the time.

The fetal movement information processing method as claimed in claim 14 of the present invention includes the step of deleting fetal movement signals and measuring fetal movement amounts based on stop by a switch or input of event marker which can be operated by a pregnant woman.

Effect of the Invention

A fetal movement information processing device and a fetal movement information processing method according to the present invention are able to record, for example, accurate fetal movement information for a long time during maternal sleep overnight of a pregnant woman by an output signal from a passive fetal movement sensor attached to the abdomen of the pregnant woman and a passive maternal movement sensor attached to a required region of the pregnant woman, obtain fetal movement waves from which the influence of maternal movements has been removed based on the obtained fetal movement information, and obtain fetal movement information by which a healthy growth state, namely, a well-being state, of a fetus can be accurately grasped or predicted by performing fetal movement primary processing for extracting wave information selected with slice levels and/or slice times which are required thresholds set in advance for the fetal movement waves and by displaying the fetal movement information so as to correspond to pregnancy weeks of the pregnant woman.

Furthermore, a fetal movement information processing device and a fetal movement information processing method according to the present invention detect, after the fetal movement information primary processing, types of fetal movement including those occurring for a few minutes at intervals of two or three seconds such as "hiccups" and those occurring singly such as "kicks" and "rolls" by a fetal movement type determining means. Next, the fetal movement information processing device and the fetal movement information processing method perform processing for measuring fetal movement amounts with such types of fetal movement, performs fetal movement information secondary processing for storing the result of the measuring processing as data per unit time, graphically displays the fetal movement information to correspond to pregnancy weeks of the pregnant woman, and are thereby able to obtain fetal movement information by which a healthy growth state, namely, a well-being state, of a fetus can be more accurately grasped or predicted.

In this case, it becomes possible to more accurately grasp or predict a healthy growth state, namely, a well-being state, of the fetus by making fetal movement type determination based on the wave information.

Furthermore, when a sensor for detecting respiration and the like of a pregnant woman along with a movement of the pregnant woman is used as the maternal movement sensor, the influence of biological phenomena of the pregnant woman included in output signals of the fetal movement sensor can be easily removed and the accuracy of detecting fetal movement information can be increased. All system configuration means except a fetal movement sensor 11 and a maternal movement sensor 12 of a fetal movement information processing system according to the present invention can be constructed and put into practice by a computer system.

In particular, a fetal movement information processing device and a fetal movement information processing method according to the present invention accumulate the result of the fetal movement information secondary processing as fetal movement information about fetal movement amounts per unit time for each of the pregnancy weeks of many pregnant women to construct a database, set the mean value and the standard deviation of the numbers of fetal movements for each of the pregnancy weeks of the pregnant women by the database, graphically display fetal movement information including detected fetal movement amounts per unit time to correspond to the mean value and the standard deviation of the numbers of fetal movements for each of the pregnancy weeks of the pregnant women based on the database, and are thereby able to obtain fetal movement information by which a healthy growth state, namely, a well-being state, of a fetus can be more accurately grasped or predicted.

In this case, an abnormal condition of a fetus can be confirmed easily and early by making a setting so that alarm display is made when the fetal movement information including the number of fetal movements per unit time extremely deviates, in comparison with the mean value and the standard deviation of the numbers of fetal movements for each of the pregnancy weeks of the pregnant women, from the mean value and the standard deviation.

Furthermore, a fetal movement information processing device and a fetal movement information processing method according to the present invention set a configuration including a fetal movement sensor, a maternal movement sensor, a timer, and a detected information storage means for storing signal information including fetal movement signals and maternal movement signals detected by the sensors along with time information as a fetal movement/maternal movement signal collecting device such as a portable terminal device, and sets a configuration including a fetal movement information primary processing means obtaining fetal movement information from which the influence of maternal movements has been removed based on detected information stored in the detected information storage means of the signal collecting device, a fetal movement information secondary processing means which extracts fetal movement information selected with slice levels and/or slice times which are required thresholds which have been set in advance for the fetal movement information to make fetal movement type determination and measures the fetal movement amounts of the obtained fetal movement information, and a display/output means which arranges, displays, and outputs the measured fetal movement amounts for each of pregnancy weeks corresponding to pregnancy days counted from the conception day of the pregnant woman as a fetal movement information processing device such as a main computer, so that fetal movement information for a long time can be stored in a small capacity storage means and collected easily at home. In particular, the fetal movement information processing device can be used as an effective device for a high risk pregnant woman in preeclampsia or the like. In addition, a reduction in fetal movement is recognized in advance for unexplained death of a fetus in uterus occurring at home, so that the fetal movement information processing device can be used as an effective device for finding such situation at an early stage.

Thus, a fetal movement information processing device and a fetal movement information processing method according to the present invention are able to appropriately detect and record information about fetal movements to obtain fetal movement information useful for accurately grasping or predicting a growth state, namely, a well-being state, of the fetus. In particular, the fetal movement information processing device and the fetal movement information processing method have an effect of removing the anxiety of a primiparous pregnant woman because fetal movement signals are recorded for a long time during sleep. The fetal movement information processing device can be expected to prevent bad influence on a fetus due to mental instability of a pregnant woman by reliving the anxiety and therefore can be used as a simple fetal movement monitoring device for home use. In other words, the fetal movement information processing device enables a healthy pregnant woman to do domestic management of a fetus with safety and peace of mind under the supervision of a doctor.

In addition, the fetal movement information processing device and the fetal movement information processing method make it easy to find an abnormal condition of a fetus in a uterus early and are able to transfer fetus information to a doctor appropriately and promptly with respect to a pregnant woman having a risk factor, and thereby when an abnormal condition is found, the domestic management is promptly changed to management in a hospital and appropriate treatment can be done promptly, so that the device and the method are useful for making the management in a hospital efficient and improving the credibility of the medical care.

Furthermore, a fetal movement information processing device and a fetal movement information processing method according to the present invention can be set so as to distinguish maternal movement signals clearly to detect appropriate fetal movement signals by providing a switch as an event marker which generates event signals for distinguishing maternal movement signals influencing fetal movement signals.

Furthermore, a fetal movement information processing device and a fetal movement information processing method according to the present invention use an electrical capacitance acceleration detection type sensor having a structure with a weight pasted on a movable film and are thereby able to set appropriate conditions suitable for the frequencies of fetal movements, improve the sensitivity of detection of fetal movement signals, and reduce inclusion of pregnant woman's biological signals as much as possible. In addition, the device and the method use a maternal movement sensor and are thereby able to appropriately remove maternal movement signals overlapping fetal movements to achieve accurate detection of fetal movement signals easily.

BRIEF DESCRIPTION OF THE DRAWINGS

FIG. 15 is an explanatory diagram showing fetal movement signals before and after a fetus moves and ultrasound tomographic images of the fetus measured in synchronization with the fetal movement signals; and FIG. 16 shows a recorded waveform chart of fetal movements during sleep of a pregnant woman (37 weeks) and a progress chart of fetal movements and maternal movements overnight by the fetal movement information processing device according to the present invention.

BEST MODES FOR CARRYING OUT THE INVENTION

Next, embodiments of a fetal movement information processing device and a fetal movement information processing method according to the present invention will be described in detail below with reference to the accompanied drawings.

First Embodiment

Figure 1:
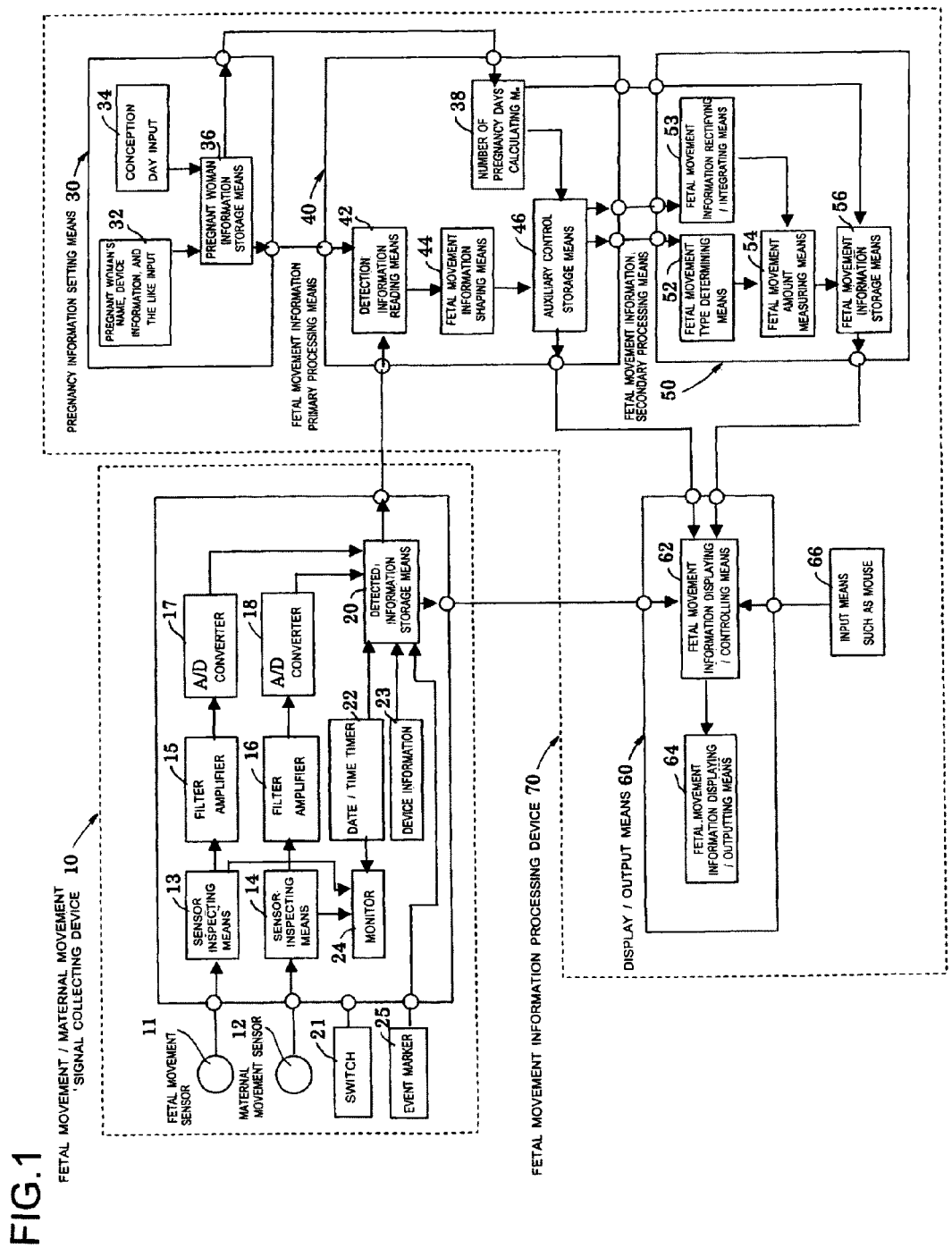
FIG. 1 is a system configuration diagram showing a first embodiment of a fetal movement information processing device according to the present invention.

FIG. 1 shows an embodiment of the system configuration of a fetal movement information processing device and a fetal movement information processing method according to the present invention. The fetal movement information processing system shown in FIG. 1 includes a fetal movement/maternal movement signal collecting device 10 which has been set to collect and store fetal movement signals and maternal movement signals and a fetal movement information processing device 70 including a main computer and the like which are set to perform processing of fetal movement information based on the fetal movement signals and the maternal movement signals collected and stored by the fetal movement/maternal movement signal collecting device 10. The fetal movement information processing device 70 includes a pregnancy information setting means 30, a fetal movement information primary processing means 40, a fetal movement information secondary processing means 50, and a display/output means 60.

The fetal movement/maternal movement signal collecting device 10 includes a fetal movement sensor 11 and a maternal movement sensor 12, sensor inspecting means 13 and 14, filter amplifiers 15 and 16, and A/D converters 17 and 18 which correspond to the sensors 11 and 12 respectively, a switch 21 which is a push-button switch or the like for controlling the operation of the device 10, a timer 22 for setting and input of date and time, a device information input means 23 for setting and input of device information for matching with fetal movement information processing device 70, and a detected information storage means 20 in which fetal movement signals and maternal movement signals detected by the sensors are input and stored.

In addition, with respect to inspection information obtained by the sensor inspecting means 13 and 14, a monitor 24 is provided which is capable of displaying a fetal movement detection signal detected by the fetal movement sensor in association with detection time information indicating times when the fetal movement signals are detected and capable of monitoring whether the fetal movement sensor is normally operating or not. Furthermore, in this embodiment, besides the switch 21 for controlling the operation of the device 10, an event marker 25 including a switch and the like which can be operated by a pregnant woman is provided, so that event marks are added, when the pregnant woman moves intentionally, to fetal movement signals so as to be able to exclude determination as fetal movement signals.

The fetal movement sensor 11 includes an electrical capacitance acceleration detection type sensor and outputs a signal x(t) the voltage of which varies according to movements of a fetus. The maternal movement sensor 12 also includes an electrical capacitance acceleration detection type sensor and outputs a signal y(t) the voltage of which varies according to movements of the pregnant woman. The sensors 11 and 12 are each generally provided with an amplifier inside it, but may be configured so that the output signals of the sensors 11 and 12 are amplified by filter amplifiers 15 and 16 provided externally.

The filter amplifiers 15 and 16 are preferably, for example, a low-pass filter having a cut-off frequency of 100 Hz (changed to 50 Hz and 30 Hz) and an attenuation factor of 12 dB/oct, and a high-pass filter having a cut-off frequency of 20 Hz (changed to 5 Hz) and an attenuation factor of 12 dB/oct, respectively.

The electrical capacitance acceleration detection type sensor is preferably an acceleration detection type sensor configured to have a weight pasted on a movable film, which is described in Japanese Unexamined Patent Publication No. 2003-52690 and developed by the present inventor et al. In other words, a common microphone type sensor for sound collection has a disadvantage of being easy to receive noise caused by cardiac sound of a pregnant woman, contact between the pregnant woman's body and any object, and rubbing sound of clothes and the like. The acceleration detection type sensor having a weight pasted on a movable film, which catches the movement of the weight pasted on the movable film caused by an impact to the pregnant woman's body surface given when the fetus moves, is able to detect only acceleration components accurately.

In this case, as the movable film of the electrical capacitance acceleration detection type sensor, a film which is a metal film or made of metal deposited polymeric material or an electret film in which electric charges have been injected in advance can be used. When the electrical capacitance acceleration detection type sensor has a structure with, for example, a movable film having the diameter of 20 mm on which a weight having the diameter of 13 mm and the weight of 1 to 3 g is pasted, it was confirmed that an output voltage of 650 to 800 mV is obtained for the vibration acceleration of 0.1 G and a stable frequency characteristic is obtained between 5 Hz and 100 Hz and therefore the sensor has a very good sensitivity as the fetal movement sensor and is effective on detection and measurement of fetal movement signals.

Figure 2:
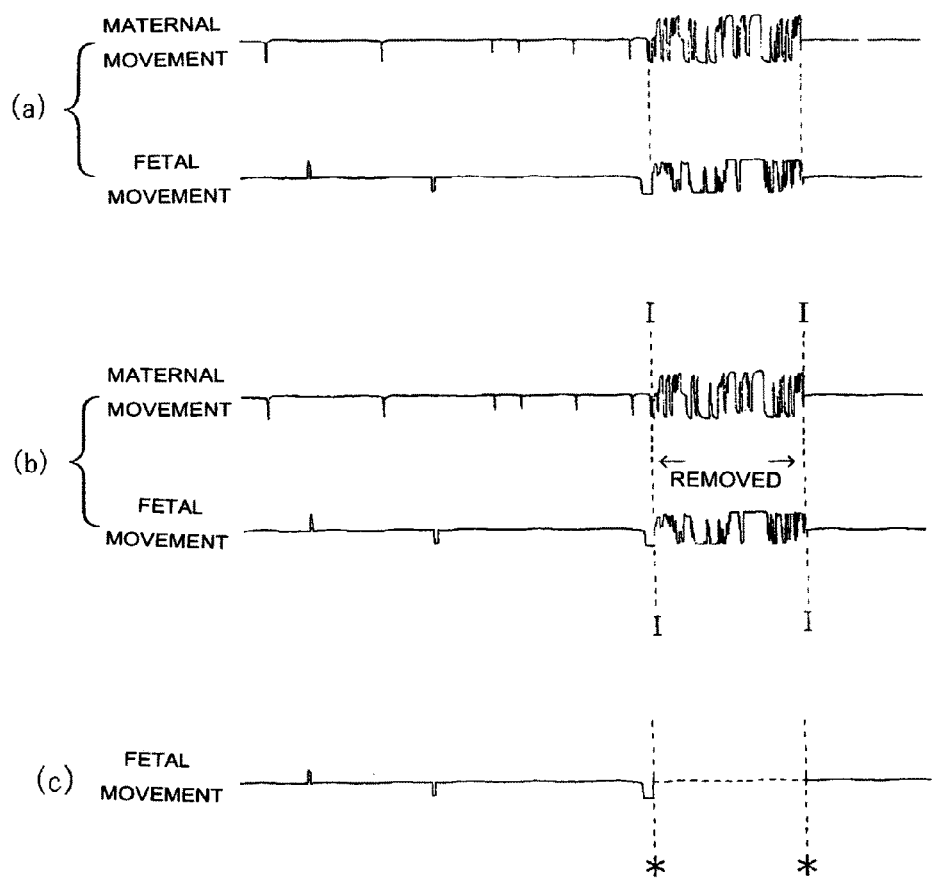
FIGS. 2(a) to 2(c) are waveform charts showing the state of processing of fetal movement signals and maternal movement signals processed by a fetal movement waveform shaping means of the fetal movement information primary processing means of a fetal movement information processing device according to the present invention.

The fetal movement sensor 11 and the maternal movement sensor 12 are inspected for the normal operations of the sensors 11 and 12 by the sensor inspecting means 13 and 14. When the sensors 11 and 12 are operating normally, the output signal x(t) of the fetal movement sensor 11 and the output signal y(t) of the maternal movement sensor 12 are sampled with a predetermined sampling frequency fs (frequency twice or more as much as the upper limits of the frequency bands of the output signals of the sensors 11 and 12) by the filter amplifiers 15 and 16 and the A/D converters 17 and 18, and are converted to digital sampling values X(k) and Y(k), respectively, which are input to the detected information storage means 20 in order. In this case, detected information including fetal movement signals and maternal movement signals stored in the detected information storage means 20 is, for example, as shown in FIG. 2(a).

The detected information storage means 20 stores the sampling values X(k) and Y(k) with the same timing based on time information TD output from the timer 22. As the detected information storage means 20, a SRAM, a rewritable flash ROM or the like, or each type of removable card memory or USB memory may be used. A rewritable disk may also be used as a storage medium.

In this way, detected information including fetal movement signals and maternal movement signals collected by the fetal movement/maternal movement signal collecting device 10 is read by the fetal movement information processing device 70, and fetal movement information processing is performed.

In the fetal movement information processing device 70, a pregnancy information setting means 30 includes an input means 32 for input and setting of the name of a pregnant woman, aforementioned device information, and the like, a conception day input means 34 for input and setting of the conception day of the pregnant woman, and a pregnant woman information storage means 36 storing these pregnant woman information. The pregnant woman information stored in the storage means 36 is transferred to a number of pregnancy days calculating means 38 for transferring information to a fetal movement information primary processing means 40 and a fetal movement information secondary processing means 50 which will be described later, and then the number of pregnancy days is calculated by the number of pregnancy days calculating means 38.

The fetal movement information primary processing means 40 includes a detected information reading means 42 which reads fetal movement signals and maternal movement signals which have been collected with the same timing as shown in FIG. 2(a), a fetal movement information shaping means 44 which compares the fetal movement signals and the maternal movement signals which have been read by the detected information reading means 42 and removes the influence of maternal movements from fetal movement signals influenced by maternal movements as shown in FIGS. 2(b) and 2(c), and a fetal movement information auxiliary control storage means 46 for selectively moving to two or more processings for temporarily storing fetal movement information shaped by the fetal movement information shaping means 44 and measuring fetal movement amounts from the stored fetal movement information.

Figure 4:
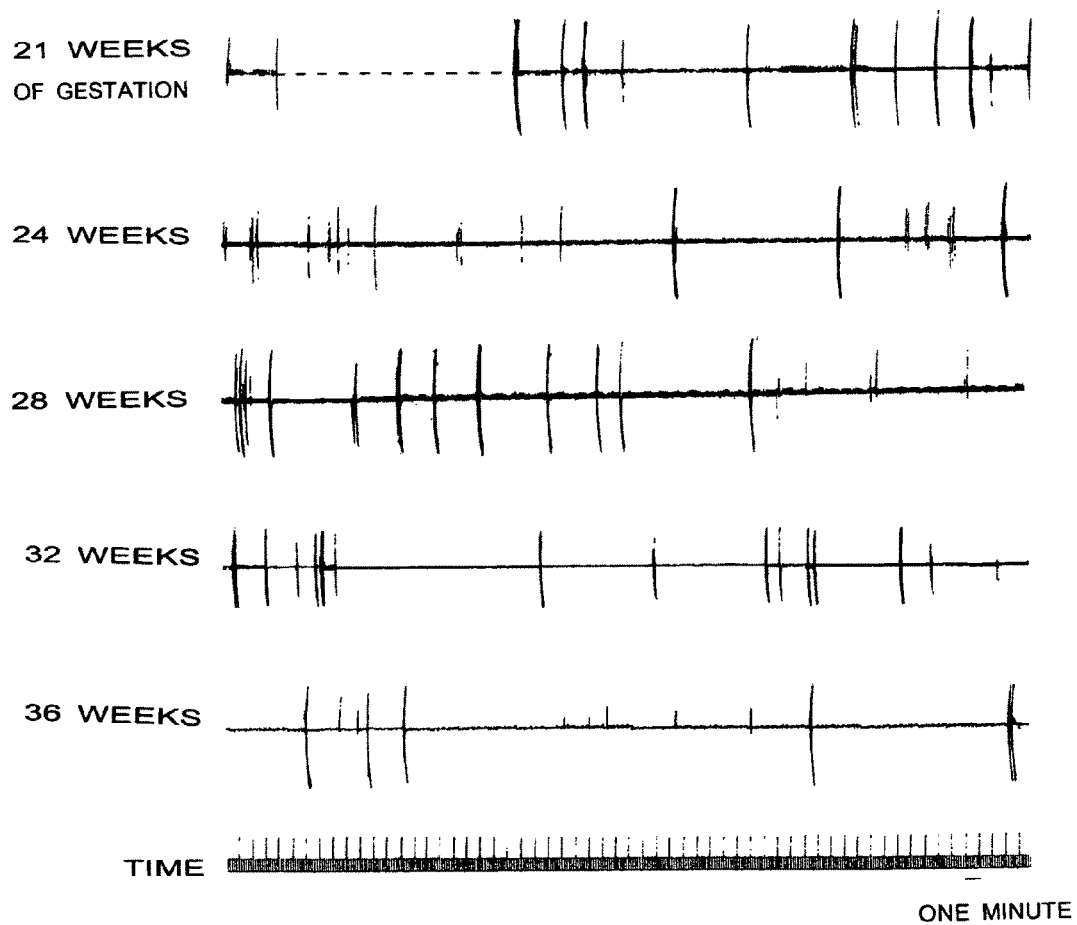
FIG. 4 is a waveform chart showing a display example of fetal movement information processed by a fetal movement type determining means of a fetal movement information secondary processing means of the fetal movement information processing device according to the present invention.

However, in this embodiment, fetal movement information which has been subjected to the primary processing described above and stored in the fetal movement information auxiliary control storage means 46 can be displayed and printed out by the display/output means 60 (FIG. 2(c)). In this case, the fetal movement information is arranged so as to correspond to the number of pregnancy weeks of the pregnant woman through a fetal movement information displaying/controlling means 62 and is displayed as shown in, for example, FIG. 4, by a fetal movement information display/output means 64. The fetal movement information displaying/controlling means 62 is able to read out detected information (see FIG. 2(a)) stored in the detected information storage means 20 before the primary processing and let the fetal movement information display/output means 64 to display the detected information. As the fetal movement information display/output means 64, for example, a liquid crystal display, a printer, or the like can be used. Furthermore, the display/output means 60 is provided with an input means 66 such as a mouse capable of externally performing processing such as enlarging, reducing, and transferring of a display of fetal movement information on the fetal movement information display/output means 64.

Furthermore, in this embodiment, fetal movement information obtained by the fetal movement information primary processing means 40 is output to the fetal movement information secondary processing means 50, which performs secondary processing of the fetal movement information.

The fetal movement information secondary processing means 50 includes a fetal movement type determining means 52 which makes fetal movement type determination with respect to fetal movement information which has been shaped by the fetal movement information shaping means 44 of the fetal movement information primary processing means 40 and stored in the fetal movement information auxiliary control storage means 46, a fetal movement information rectifying/integrating means 53 which rectifies and integrates the fetal movement information to obtain fetal movement amounts, a fetal movement amount measuring means 54 which measures the fetal movement amounts obtained by the fetal movement type determining means 52 or the fetal movement information rectifying/integrating means 53, and a fetal movement information storage means 56 which stores fetal movement information as the fetal movement amount measured by the fetal movement amount measuring means 54.

Figure 3:
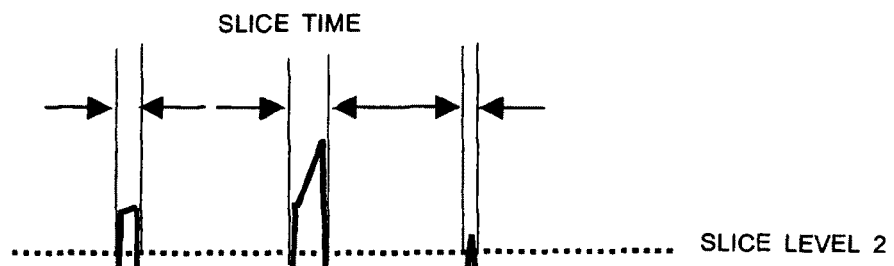
FIG. 3 is a waveform chart showing a display example of fetal movement information which is displayed by the fetal movement information display/output means of the fetal movement information processing device according to the present invention, processed by the fetal movement information primary processing means, and controlled by fetal movement information displaying/controlling means to be output and displayed.

In this case, the fetal movement type determining means 52 extracts, as shown in FIG. 3, fetal movement information with slice levels and/or slice times which are adjustable thresholds which have been set in advance from fetal movement information shaped by the fetal movement information shaping means 44, and the extracted fetal movement information can be measured as the number of fetal movements per unit time by the fetal movement amount measuring means 54. In other words, by the fetal movement type determining means 52, slice levels SL1 and SL2 and a slice time ST which are predetermined thresholds are set as shown in FIG. 3 and the state of occurrence of fetal movements can be therefore confirmed. Thus, signals extracted by the slice levels SL1 and SL2 and the slice time ST which have been set as described above can be each counted and measured as the number of fetal movements per unit time. These levels can be adjusted and set manually as appropriate.

Figure 5:
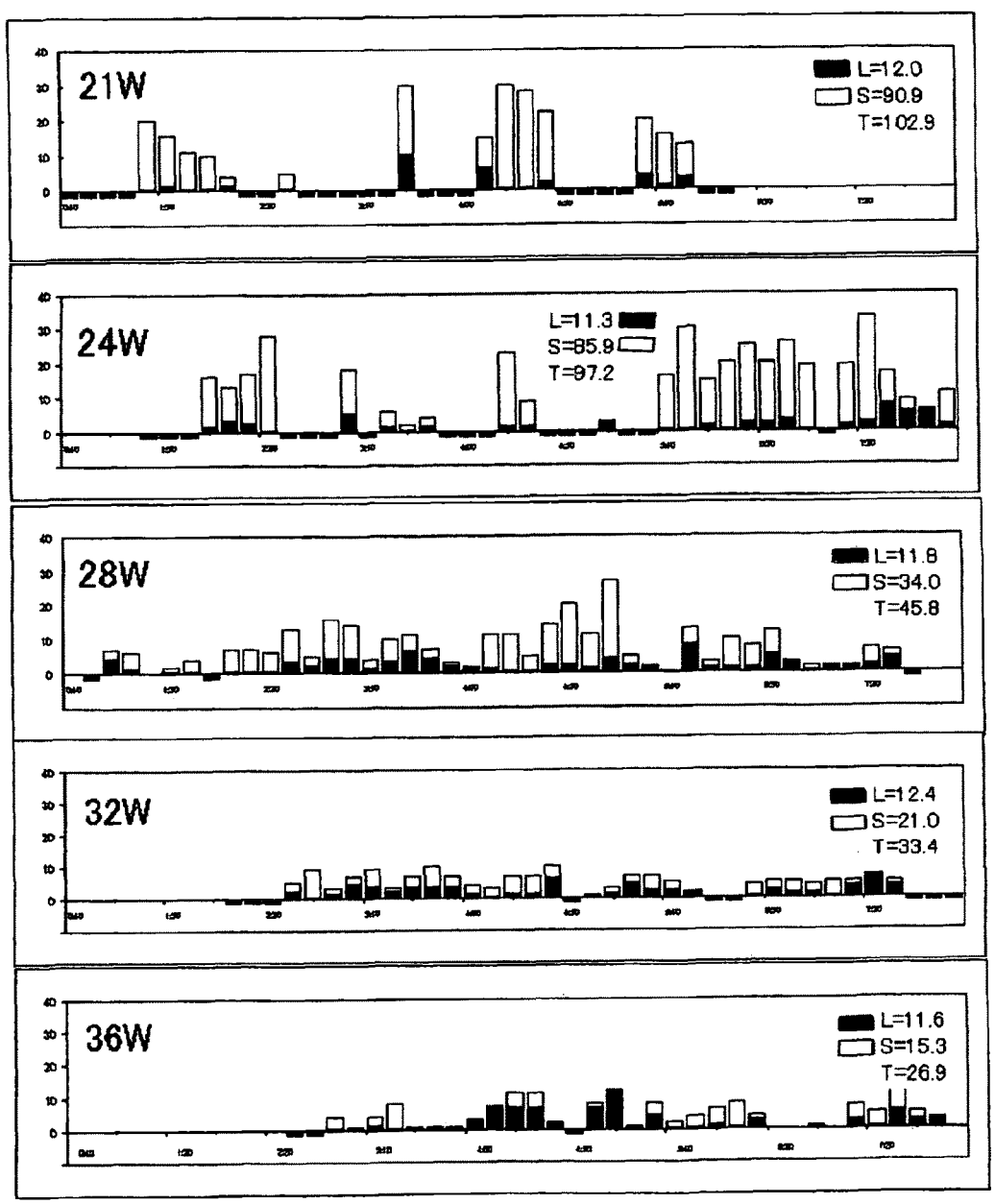
FIG. 5 is an explanatory diagram showing an example of graphical display of fetal movement amounts per unit time classified and measured by type of fetal movement determined by the fetal movement type determining means of the fetal movement information secondary processing means of the fetal movement information processing device according to the present invention.

The fetal movement information measured by the fetal movement amount measuring means 54 like this is organized so as to correspond to pregnancy weeks through the fetal movement information displaying/controlling means 62 of the display/output means 60 as fetal movement information including respective numbers of fetal movements per unit time, and is graphically displayed as shown in, for example, FIG. 5 by the fetal movement information displaying/outputting means 64. In this case, the number of fetal movements per unit time can be set as the number of fetal movements per unit time such as, for example, 5 minutes, 10 minutes, 20 minutes, or 30 minutes.

In the graphical display shown in FIG. 5, L represents the amount of large and slow fetal movements and large and fast fetal movements, S represents the amount of small and slow fetal movements and small and fast fetal movements, and T represents the sum of them. An amount less than zero level represents fetal movements which cannot be measured due to maternal movements, and zero level represents the state where there is no fetal movement. Thus, from the graphical display of fetal movement amounts per unit time for each of the pregnancy weeks shown in FIG. 5, a healthy growth state, namely, a well-being state, of the fetus can be grasped or predicted easily and accurately.

Figure 6:
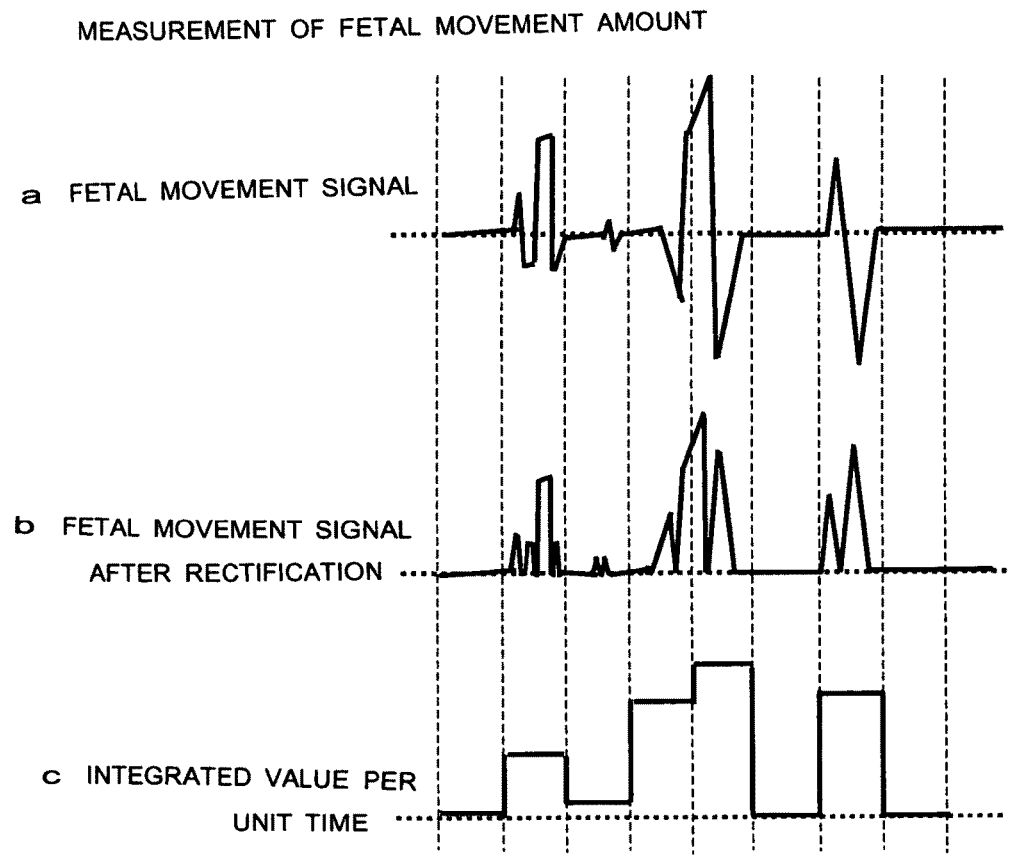
FIGS. 6(a) to 6(c) are waveform charts showing a display example of fetal movement information rectified and integrated by the fetal movement information rectifying/integrating means of the fetal movement information secondary processing means of the fetal movement information processing device according to the present invention.

Furthermore, as shown in FIG. 6, the fetal movement information rectifying/integrating means 53 rectifies the fetal movement information shaped by the fetal movement information shaping means 44 and then integrates it every predetermined unit time, and the obtained integrated values can be each measured as a fetal movement amount per unit time by the fetal movement amount measuring means 54. In other words, the fetal movement information rectifying/integrating means 53 rectifies, as shown in FIG. 6(b), fetal movement signals which have been input shown in FIG. 6(a), and then integrates them as shown in FIG. 6(c), and therefore the states of occurrence of fetal movements can be confirmed. Thus, it becomes possible to measure integrated values obtained as above as fetal movement amounts per unit time, respectively.

The fetal movement information measured by the fetal movement amount measuring means 54 like this is, as described above, organized so as to correspond to pregnancy weeks through the fetal movement information displaying/controlling means 62 of the display/output means 60 as fetal movement information including fetal movement amounts per unit time, and graphically displayed by the fetal movement information displaying/outputting means 64 (see FIG. 5).

A database is constructed by accumulating many pieces of fetal movement information about fetal movement amounts per unit time for each of the pregnancy weeks of the pregnant women, and the mean value and the standard deviation of fetal movement amounts for each of the pregnancy weeks of the pregnant women can be set by the database. In other words, based on fetal movement information about fetal movement amounts per unit time collected for each type of fetal movements and for each of the pregnancy weeks from many pregnant women in advance as shown in Table 1, the mean value and the standard deviation of fetal movement amounts for each type of the fetal movements and for each of the pregnancy weeks can be calculated to construct a database. Then, based on information from this database and fetal movement amounts measured and calculated about a pregnant woman who came to have an examination, a healthy growth state, namely, a well-being state, of a fetus can be grasped or predicted easily and accurately.

Figure 7:
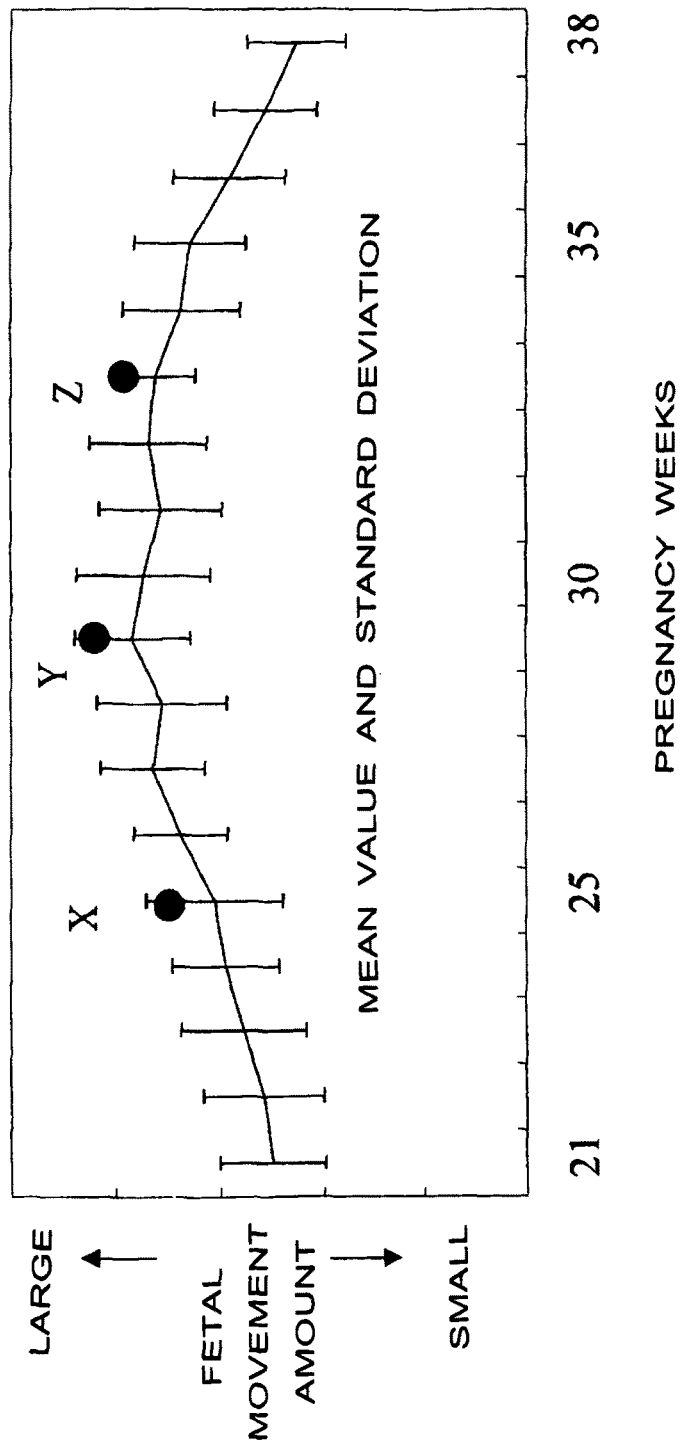
FIG. 7 is an explanatory diagram showing an example of graphically displaying fetal movement amounts per unit time measured by a fetal movement amount measuring means of the fetal movement information secondary processing means of the fetal movement information processing device according to the present invention along with mean values and standard deviations of accumulated fetal movement information.

In other words, fetal movement signals and maternal movement signals in the detected information storage means 20 of the fetal movement/maternal movement information collecting device 10 brought by the pregnant woman are read out by the detected information reading means 42 of the fetal movement information primary processing means 40, signals obtained by information processing performed through the fetal movement information shaping means 44, the auxiliary control storage means 46, and the like are stored in the fetal movement information storage means 56 of the fetal movement information secondary processing means 50, and data processing is performed for each type of fetal movements. At that time, a database related to fetal movement amounts is constructed based on fetal movement information representing fetal movement signals and fetal movement amounts collected from many pregnant women in advance. This database also includes information about mean values and standard deviation values of fetal movement amounts for each type of fetal movements. The mean values and the standard deviation values of the fetal movement information are compared and combined for each of pregnancy weeks, with fetal movement information including fetal movement amounts per unit time about the pregnant woman who has come to the hospital, and the combined result is displayed. For example, as shown in FIG. 7, the fetal movement amounts of the pregnant woman are graphically displayed like X, Y, and Z by the display/output means 60. In this case, it becomes possible to make a setting so that alarm display, for example, is made when the fetal movement information seems to deviate from its mean value and standard deviation remarkably. In FIG. 7, in the case of Z, the fetal movement information seems to deviate from the standard deviation value range. Like this, it becomes possible to grasp or predict a well-being state of a fetus easily and accurately by graphically displaying fetal movement amounts.

Figure 8:
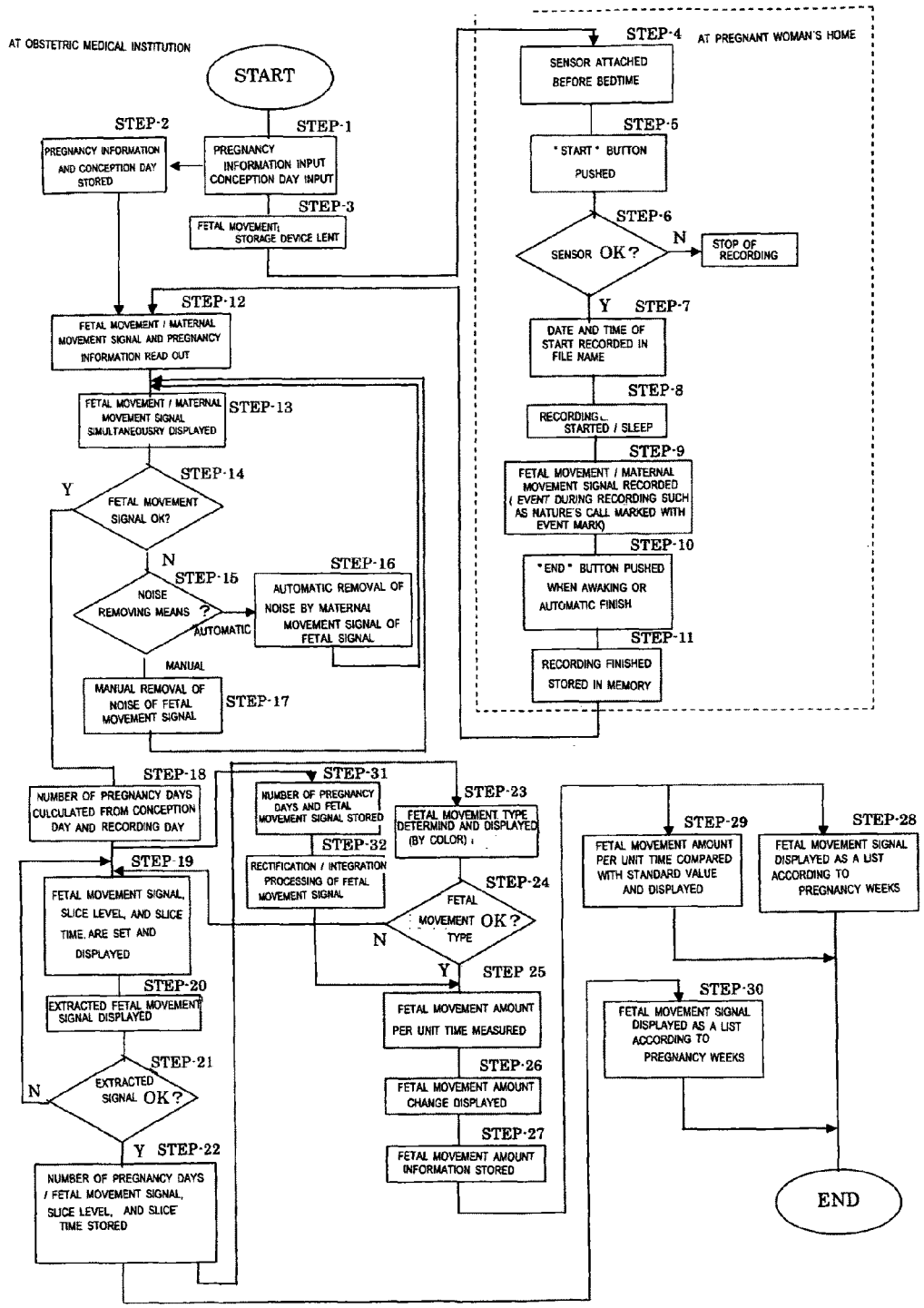
FIG. 8 is a flow chart showing an operation program for the first embodiment of the fetal movement information processing device according to the present invention.

FIG. 8 is a flow chart showing an operation program of the fetal movement information processing device of this embodiment shown in FIG. 1. The operation of the fetal movement information processing device of this embodiment shown in FIG. 1 will be described below with reference to this flow chart.

When the fetal movement information processing device of this embodiment is used, pregnancy information of a pregnant woman is set at the start of the operation of it at an obstetric medical institution. In other words, the pregnancy information including pregnant woman information and device information is input to and stored in the fetal movement/maternal movement signal collecting device 10 and the fetal movement information processing device 70 (STEP-2). After that, the fetal movement/maternal movement signal collecting device 10 is lent to the pregnant woman (STEP-3).

The device 10 lent to the pregnant woman records fetal movements at her home. Before bedtime, the fetal movement sensor 11 and the maternal movement sensor 12 are attached to the pregnant woman (STEP-4), and the "start" button of the switch 21 of the device 10 is pushed (STEP-5). As a result, the operation of the device 10 starts, and the normal states of the sensors are confirmed and inspected by the sensor inspecting means 13 and 14 (STEP-6). When any of the sensors is not normal, the operation is stopped immediately. When each of the sensors is normal, date and time are recorded in a file name (STEP-7), recording of a fetal movement detection signal and a maternal movement detection signal from the respective sensors is started (STEP-8), and the signals are continuously recorded while the pregnant woman is sleeping (STEP-9). In this connection, when the pregnant woman temporarily awakes by nature's call, roll-over, or the like while sleeping, she is able to attach event marks to fetal movement signals being recorded by operating the event marker 25. The operation of the device 10 is finished by pushing the "end" button when the pregnant woman awakes or automatically (STEP-10). In this way, fetal movement signals and maternal movement signals overnight are recorded and stored in a memory as the detected information storage means 20 of the device 10 (STEP-11). After that, as with the above, fetal movement signals and maternal movement signals are recorded and stored repeatedly according to the number of pregnancy weeks of the pregnant woman, and the respective records of the signals are accumulated.

When the records of the fetal movement signals and the maternal movement signals have been accumulated like this, the device 10 or only the memory is brought to the obstetric medical institution by judgment of the pregnant woman or at a periodical medical examination as appropriate, and then the fetal movement signals and the maternal movement signals are read out with the pregnancy information by the fetal movement information processing device 70 (STEP-12). The device 70 displays the fetal movement signals and the maternal movement signals at the same time (STEP-13) and it is determined whether each of the fetal movement signals is appropriate or not (STEP-14). When a fetal movement signal is not appropriate by the influence of a maternal movement signal, an automatic or manual operation for noise removal, that is, operation for shaping of the fetal movement signal is selected (STEP-15). In general, an automatic operation for noise removal is selected at first, and an operation of automatically removing noises of fetal movement signals overlapping maternal movement signals generated continuously during a fixed period of time based on and after generation of a fetal movement signal is performed (STEP-16). Fetal movement signals obtained after automatic noise removal like this are displayed simultaneously with the maternal movement signals (STEP-13), and it is determined again whether the fetal movement signals are appropriate or not (STEP-14). The above operations are repeated, and when noise removal is still insufficient, a manual operation of noise removal is performed (STEP-17) to make the fetal movement signal appropriate.

In relation to STEP-13, FIG. 16 shows the result of recording of fetal movements of a pregnant woman (26 years old, 37 weeks of gestation) to whom the fetal movement sensor and the maternal movement sensor were attached before bedtime, which was obtained using a fetal movement information processing device and the processing method thereof according to the present invention. In this case, the fetal movement sensor was attached to a place where the fetus had often moved with a double-face tape and a surgical tape and the maternal movement sensor was attached to her thigh in the same way. Then the pregnant woman went to bed at 0:57. After she had got up at 8:07, the sensors were removed. In FIG. 16, the lower two waveform charts show the maternal movement signals and the fetal movement signals during sleep along with a time line (elapsed time line). The upper waveform charts in FIG. 16 show enlarged maternal movement signals and fetal movement signals at a time (6:25) indicated by an arrow (cursor K) which was marked on the lower time line (the time can be designated by moving the cursor K with the input means 66 such as a mouse). From this result, a fetal movement in a state that there is no movement of the pregnant woman was clearly confirmed at three points of time. Some heart beat waveforms having small amplitude of the pregnant woman were observed in the fetal movement sensor's chart.

When appropriate fetal movement signals have been obtained as described above, number of pregnancy days is calculated from the conception day and the day when the fetal movements were recorded which were input to the device 70 (STEP-18), the processing of extracting the fetal movement signals is performed with slice levels and/or slice times which are required thresholds which have been set in advance for the fetal movement signals (STEP-19), and the extracted fetal movement signals are displayed as appropriate (STEP-20). In this case also, it is determined whether the extracted fetal movement signals are appropriate or not (STEP-21). When the fetal movement signals are appropriate, they are stored with the number of pregnancy days, the slice levels, and the slice times (STEP-22). When the fetal movement signals are not appropriate, the thresholds of the slice levels and/or slice times are adjusted and then the processing of extracting the fetal movement signals is repeated (STEP-19 to STEP-21). With respect to the fetal movement information obtained in this way, fetal movement type determination is made by the fetal movement type determining means 52 (STEP-23) and it is confirmed whether the fetal movement type determination is appropriate or not (STEP-24). In this case, the fetal movement type determination can be made easy by using different color for each type of fetal movements when they are displayed and output. Furthermore, when the result of the fetal movement type determination is not appropriate, the thresholds of the slice levels and/or slice times are adjusted and the processing of extracting the fetal movement signals is repeated (STEP-19 to STEP-21).

With respect to fetal movement information obtained by making fetal movement type determination in this way, fetal movement amounts per unit time are measured for each type of fetal movements (STEP-25). The fetal movement amounts per unit time for which fetal movement type determination has been made like this are stored as fetal movement amount changes (STEP-26 and STEP-27), which are arranged to correspond to pregnancy weeks to be displayed and output (STEP-28). Furthermore, with respect to information about the fetal movement amounts, the fetal movement amounts per unit time are compared with their standard values based on the accumulated database to be displayed (STEP-28). Furthermore, the fetal movement signals stored with the number of pregnancy days, the slice levels, and the slice times (STEP-22) may be displayed as a list according to pregnancy weeks (STEP-30).

Furthermore, the appropriate fetal movement signals which have been read out from the device 10 and for which noise removal has been performed as appropriate are stored with the number of pregnancy days (STEP-18) after the number of pregnancy days is calculated from the conception day and the day when the fetal movements were recorded (STEP-31). After that, the processing of rectifying and integrating the fetal movement information is performed (STEP-32), and fetal movement amounts per unit time can be measured from the obtained integrated values of the fetal movement information (STEP-25). In this case also, subsequent storing processing and displaying/outputting processing can be performed as with the fetal movement information for which fetal movement type determination has been made (STEP-25 to STEP-29).

As a result of recording an analog signal and an image signal at the same time with respect to the state that a fetus is moving using the fetal movement information processing device of this embodiment together with the ultrasound tomography device described above, it was confirmed that record and display as shown in FIG. 15 described above are obtained.

Second Embodiment

Figure 9:
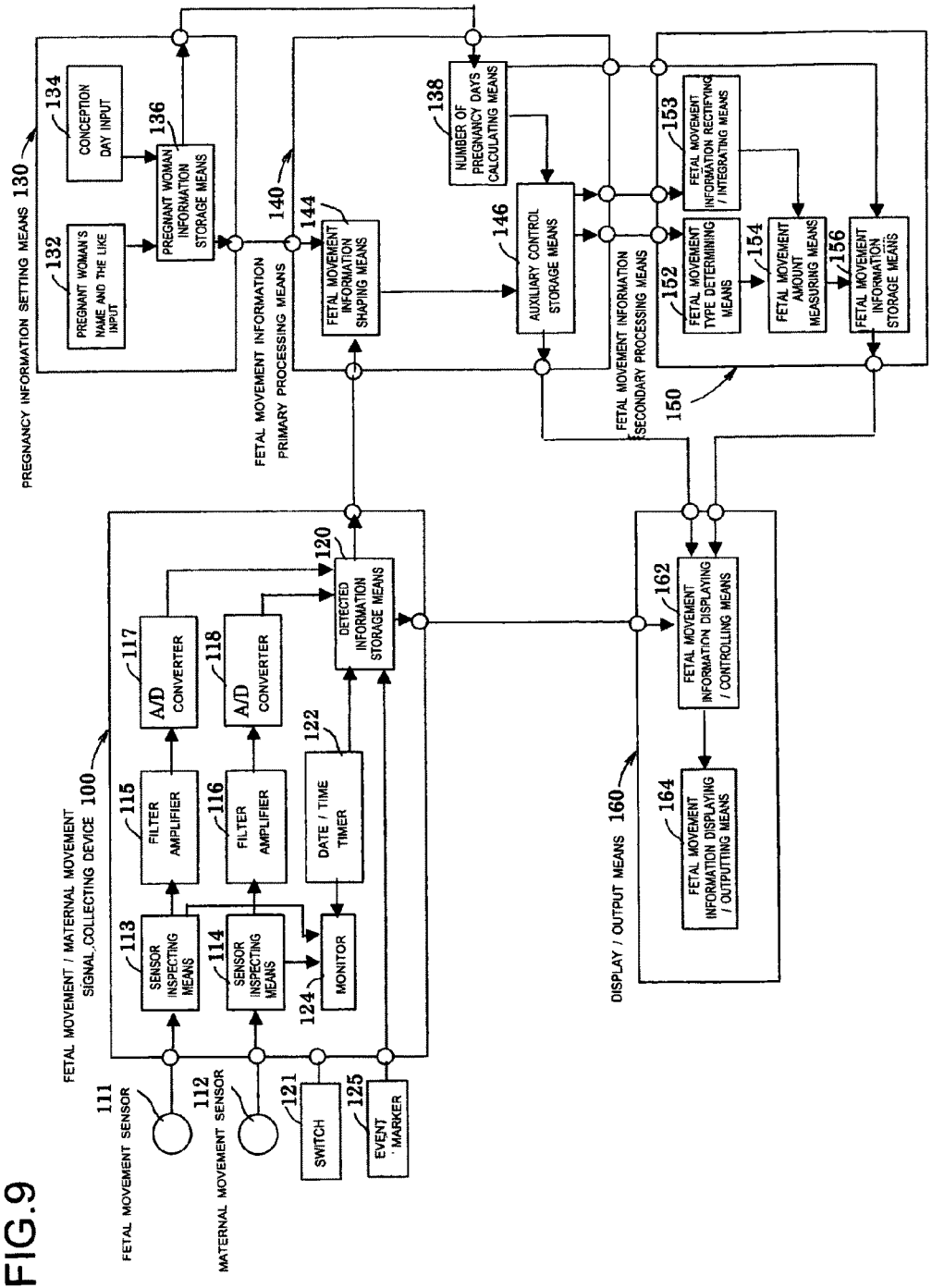
FIG. 9 is a system configuration diagram showing a second embodiment of the fetal movement information processing device according to the present invention.
Figure 10:
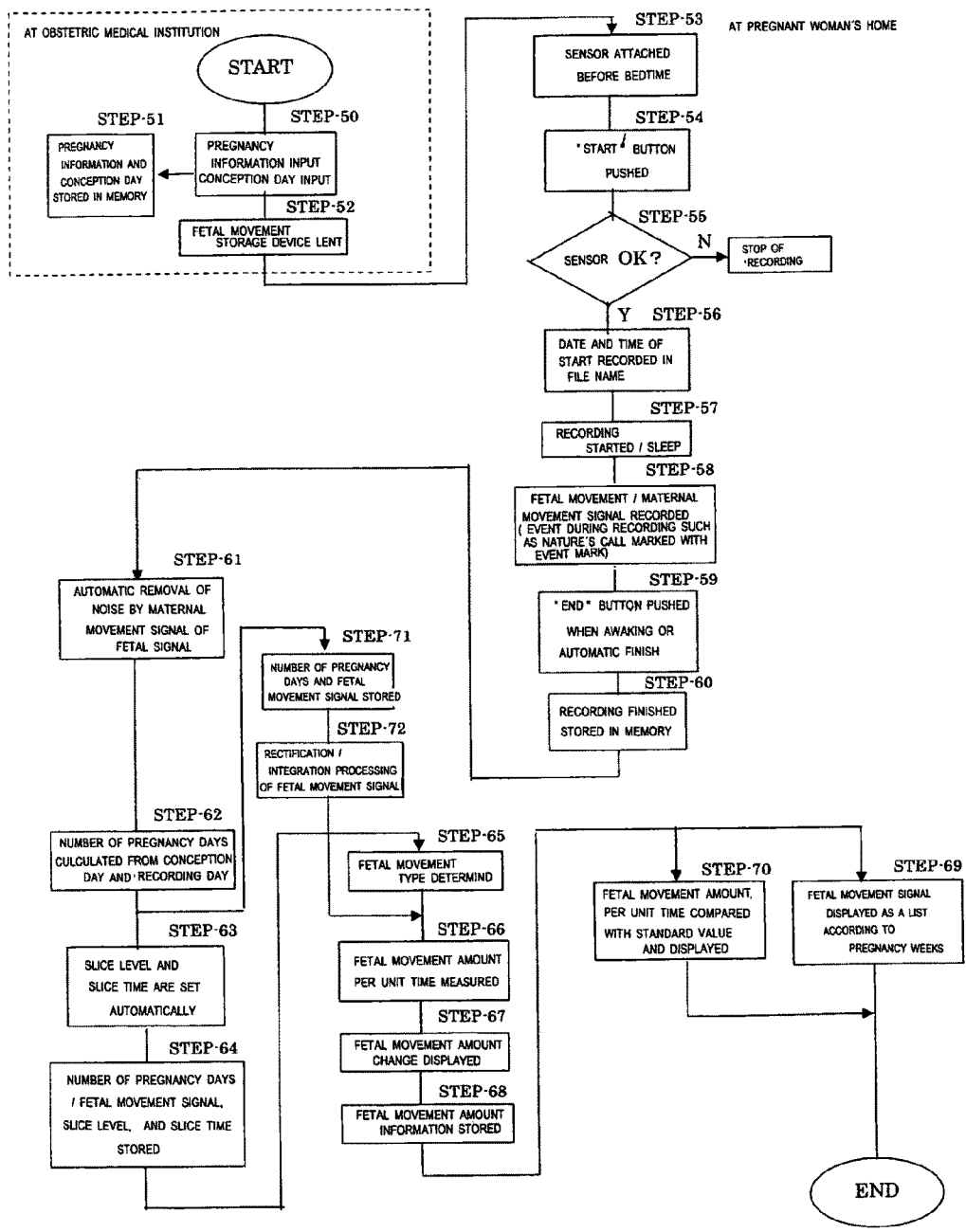
FIG. 10 is a flow chart showing an operation program for the second embodiment of the fetal movement information processing device according to the present invention.
Figure 11:
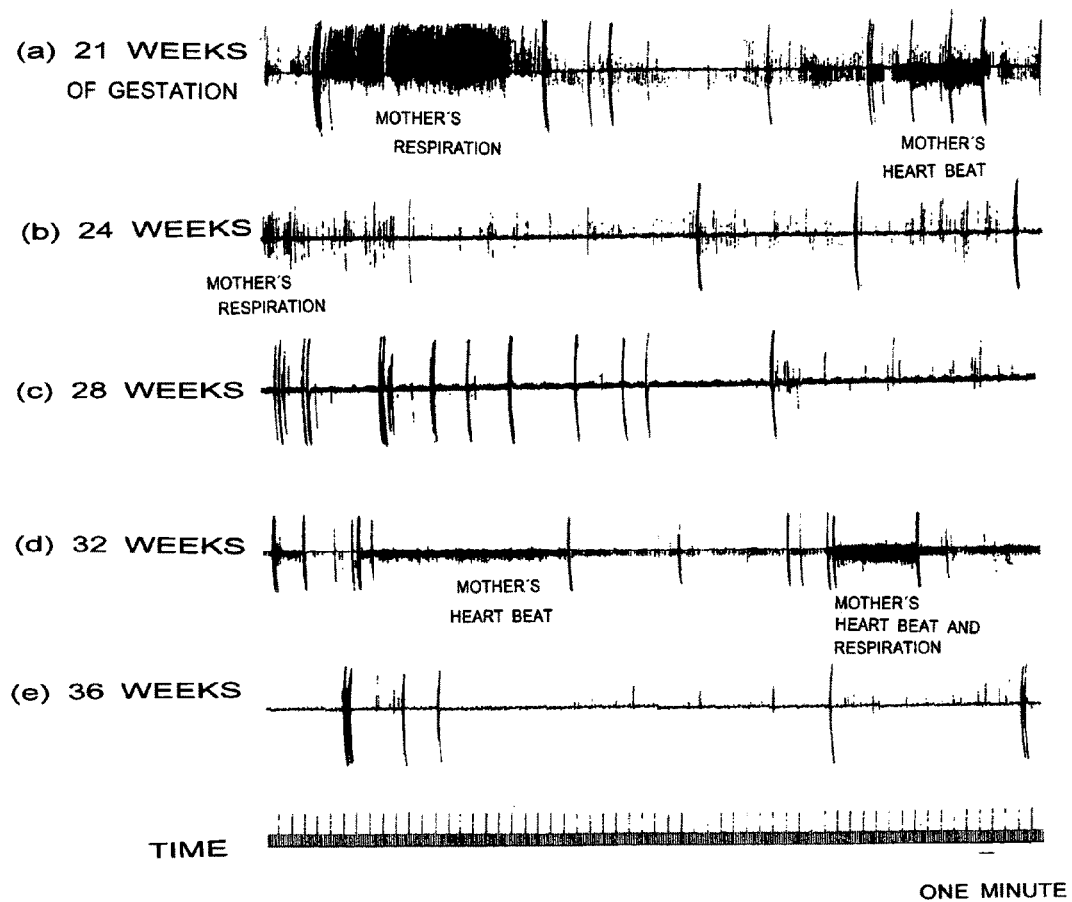
FIGS. 11(a) to 11(e) are waveform charts showing the result of measuring fetal movements in a required period of time during sleep for each of pregnancy weeks using a conventional fetal movement sensor.
Figure 12:
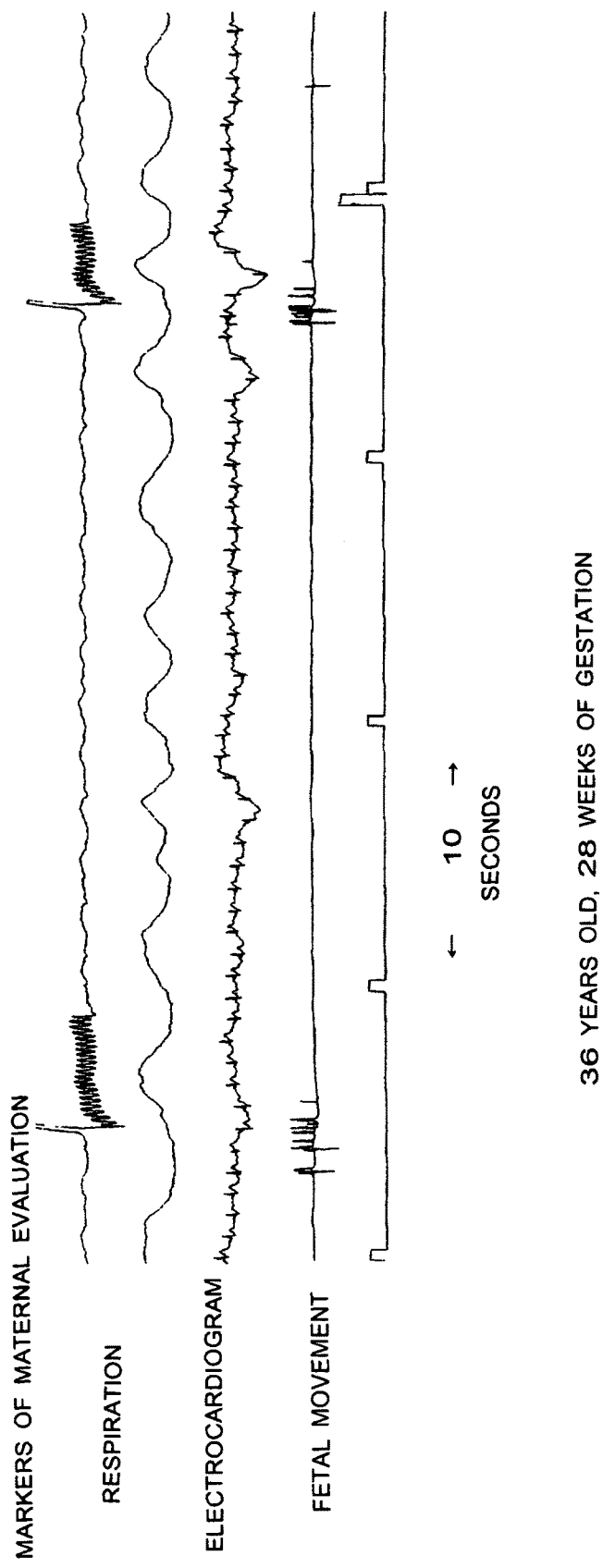
FIG. 12 shows a subjective evaluation of a pregnant woman about fetal movements when the fetal movements are measured along with respiration and an electrocardiogram of the pregnant woman during daytime wakefulness.
Figure 13:
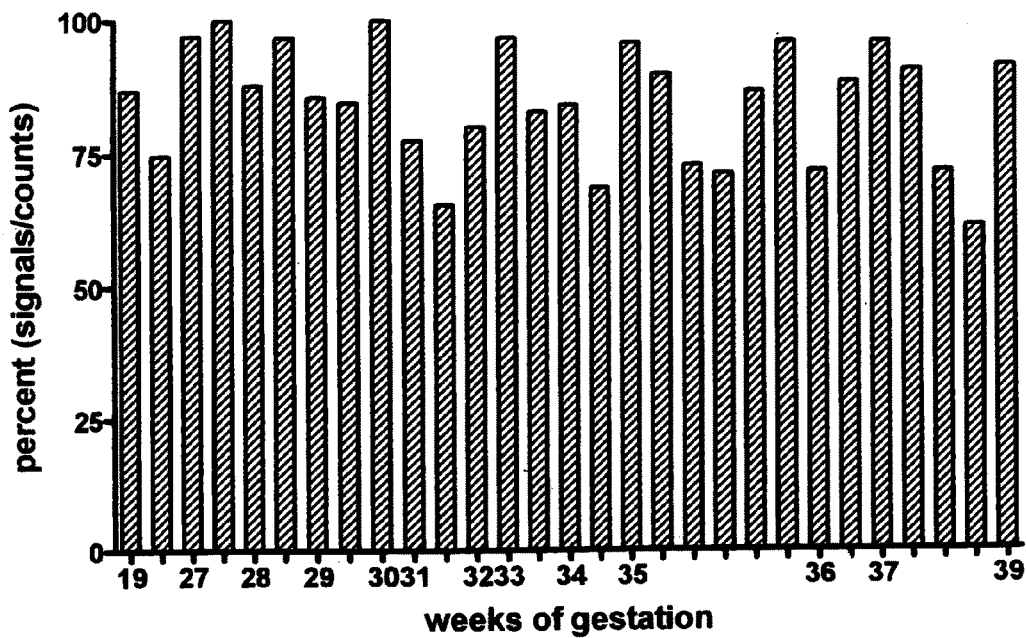
FIG. 13 is a bar chart showing the relation of agreements between subjective fetal movement evaluations and fetal movement signals of 29 pregnant women who are 19 to 39 weeks of gestation.
Figure 14:
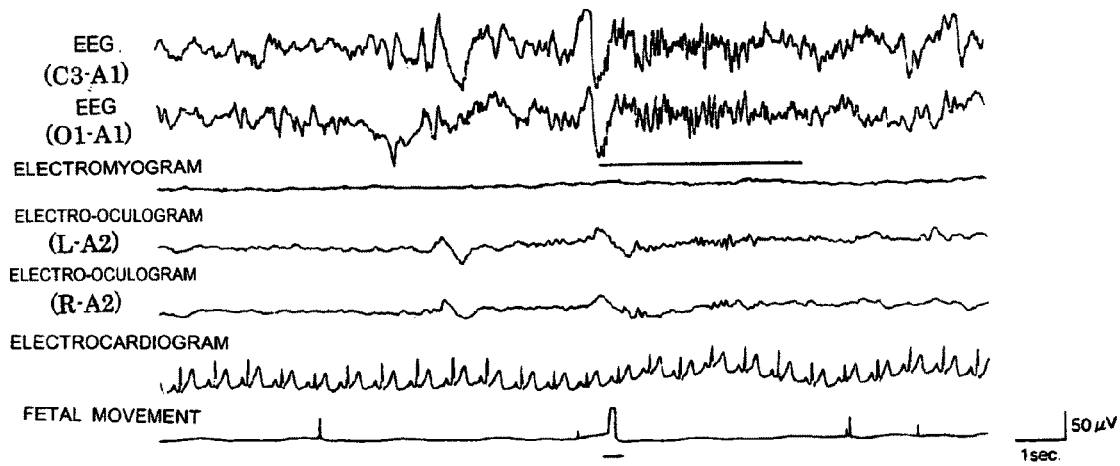
FIG. 14 is a waveform chart showing micro-arousals induced by fetal movements when the fetal movements are measured along with a polysomnography of a pregnant woman.

FIG. 9 shows another embodiment of the system configuration of a fetal movement information processing device according to the present invention. For convenience of description, the same components as those of the system configuration of the fetal movement information processing device of the first embodiment shown in FIG. 1 are each shown with the same reference symbol plus 100, and detail description about them is omitted. In other words, the fetal movement information processing device of this embodiment is configured as a device in which a fetal movement information collecting means 100 and other system components including a pregnancy information setting means 130, a fetal movement information primary processing means 140, a fetal movement information secondary processing means 150, and a display/output means 160 are integrated. Furthermore, FIG. 10 is a flow chart showing an operation program of the fetal movement information processing device of this embodiment. As is clear from FIGS. 9 and 10, the configuration and operation of the fetal movement information processing device of this embodiment are basically the same as those of the fetal movement information processing device of the first embodiment, and therefore refer to the description about the system configuration of FIG. 1 and the operation of the flow chart shown in FIG. 8.

Up to this point, the preferred embodiments of the present invention have been described, but the present invention is not limited to these embodiments. For example, the system of the first embodiment is configured so that a communication device is directly built in the fetal movement/maternal movement signal collecting device or an interface which can be connected to a communication device such as a mobile phone is provided to transmit detected information stored in the detected information storage means to an information processing device of a medical institution through a communication network. A system can be thereby realized in which the detected information is transmitted to the fetal movement information processing device of a medical institution and a doctor or the like is able to confirm transmitted fetal movement information of a pregnant woman. Furthermore, a fetal movement information processing device and a fetal movement information processing method according to the present invention can be preferably applied to domestic animals such as cows and horses. In addition, various design changes can be made within a scope not departing from the spirit of the present invention.

TABLE 1

| | Pregnancy weeks | | | |
|---|---|---|---|---|
| 21 weeks | 22 weeks | 23 weeks | ... | 40 weeks |
| Fetal Movement Type A (e.g. "roll") | | | | |
| 21DATA1 | 22DATA1 | 23DATA1 | | 40DATA1 |
| 21DATA2 | 22DATA2 | 23DATA2 | | 40DATA2 |
| 21DATA3 | 22DATA3 | 23DATA3 | | 40DATA3 |
| . | . | . | | . |
| . | . | . | | . |
| . | . | . | | . |
| 21MEAN | 22MEAN | 23MEAN | ... | 40MEAN |
| 21SD | 22SD | 23SD | ... | 40SD |
| Fetal Movement Type B (e.g. "kick") | | | | |
| 21DATA1 | 22DATA1 | 23DATA1 | | 40DATA1 |
| 21DATA2 | 22DATA2 | 23DATA2 | | 40DATA2 |
| 21DATA3 | 22DATA3 | 23DATA3 | | 40DATA3 |
| . | . | . | | . |
| . | . | . | | . |
| . | . | . | | . |
| 21MEAN | 22MEAN | 23MEAN | ... | 40MEAN |
| 21SD | 22SD | 23SD | ... | 40SD |
| Fetal Movement Type C (e.g. "Movement like hiccup") | | | | |
| 21DATA1 | 22DATA1 | 23DATA1 | | 40DATA1 |
| 21DATA2 | 22DATA2 | 23DATA2 | | 40DATA2 |
| 21DATA3 | 22DATA3 | 23DATA3 | | 40DATA3 |
| . | . | . | | . |
| . | . | . | | . |
| . | . | . | | . |
| 21MEAN | 22MEAN | 23MEAN | ... | 40MEAN |
| 21SD | 22SD | 23SD | ... | 40SD |

| Description of the Reference Symbols | |
|---|---|
| 10: | Fetal movement/maternal movement signal collecting device |
| 100: | Fetal movement/maternal movement signal collecting means |
| 11, 111: | Fetal movement sensor |
| 12, 112: | Maternal movement sensor |
| 13, 113, 14, 114: | Sensor inspecting means |
| 15, 115, 16, 116: | Filter amplifier |
| 17, 117, 18, 118: | A/D converter |
| 20, 120: | Detected information storage means |
| 21, 121: | Switch |
| 22, 122: | Date and time timer |
| 23, 123: | Device information input means |
| 24, 124: | Monitor |
| 25, 125: | Event marker |
| 30, 130: | Pregnancy information setting means |
| 32, 132: | Means for inputting pregnant woman's name, device information, and the like |
| 34, 134: | Conception day input means |
| 36, 136: | Pregnant woman information storage means |
| 38, 138: | Number of pregnancy days calculating means |
| 40, 140: | Fetal movement information primary processing means |
| 42: | Detected information reading means |
| 44, 144: | Fetal movement information shaping means |
| 46, 146: | Auxiliary control storage means |
| 50, 150: | Fetal movement information secondary processing means |
| 52, 152: | Fetal movement type determining means |
| 53, 153: | Fetal movement information rectifying/integrating means |
| 54, 154: | Fetal movement amount measuring means |
| 56, 156: | Fetal movement information storage means |
| 60, 160: | Display/output means |
| 62, 162: | Fetal movement information displaying/controlling means |
| 64, 164: | Fetal movement information display/output means |
| 66: | Input means such as a mouse |
| 70: | Fetal movement information processing device |

The invention claimed is:

1. A fetal movement information processing system comprising:
a portable terminal device comprising a fetal movement signal collecting device, the fetal movement signal collecting device including:
at least one fetal movement sensor (11, 111) for being attached to a pregnant woman's abdomen for detecting fetal movements; and
a non-transitory-type fetal movement detected information storage means (20, 120) for storing fetal movement detection signals detected by said fetal movement sensor in association with detection time information indicating times of said fetal movement detection signals, respectively;
a computer comprising a fetal movement information processing device (40, 50, 140, 150) for calculating fetal movement amounts per unit time for each of pregnancy weeks of the pregnant woman from maternal information identifying the pregnant woman and number of pregnancy days information, along with the fetal movement detection signals and the detection time information stored in the non-transitory type fetal movement detected information storage means of said fetal movement signal collecting device; and
a display/output means (60) for arranging and displaying fetal movement amounts obtained by said fetal movement information processing device in order of pregnancy weeks.

2. The fetal movement information processing system as claimed in claim 1 wherein said fetal movement signal collecting further includes:
at least one maternal movement sensor (12, 112) for being attached to a pregnant woman's abdomen for detecting maternal movements; and
said fetal movement detected information storage means (20, 120) for further storing maternal movement detection signals detected by said maternal movement sensor with said fetal movement detection signals detected by said fetal movement sensor in association with detection time information indicating detection times of the maternal movement detection signals and the fetal movement detection signals, respectively.

3. The fetal movement information processing system as claimed in claim 1 wherein the fetal movement signal collecting further comprises an inspecting unit (13, 14, 113, 114) for inspecting if the fetal movement sensor and the maternal movement sensor are each normally operating.

4. The fetal movement information processing system as claimed in claim 1, wherein the fetal movement sensor and the maternal movement sensor of said fetal movement signal collecting device are an electrical capacitance acceleration detection type sensor of a structure with a weight pasted on a movable film.

5. The fetal movement information processing system as claimed in claim 1 wherein the fetal movement detected information storage means (20, 120) of said fetal movement signal collecting device is set so as to continuously store fetal movement detection signals and maternal movement detection signals during maternal sleep overnight along with set times in said storage means.

6. The fetal movement information processing system as claimed in claim 1, wherein said fetal movement information processing device (40, 50, 140, 150) further includes:
a number of pregnancy days calculator (38, 138) for receiving fetal movement detection time information and pregnancy information for calculating pregnancy days,
a detected information reader (42, 142) for reading out a detection signal from storage information in said fetal movement detected information storage means (20, 120),
a fetal movement information shaping device (44, 144) for shaping the detection signal read out by said detected information reader to extract fetal movement signals, and
a fetal movement amount measuring device (54, 154) for measuring a fetal movement amount per unit time from fetal movement information shaped by said fetal movement information shaping device.

7. The fetal movement information processing system as claimed in claim 1 wherein said fetal movement information processing device (40) further includes:
a detected information reader (42) for reading a fetal movement detection signal detected by the fetal movement sensor and a maternal movement detection signal detected by the maternal movement sensor; and
a fetal movement information shaping device (44) for establishing association between the fetal movement signals and the maternal movement signals which have been read out by the detected information reader, removing fetal movement signals influenced by maternal movements when the output levels of the maternal movement signals stored at the same time are a fixed level or more, and for outputting fetal movement signals less influenced by maternal movements.

8. The fetal movement information processing system as claimed in claim 1 wherein said fetal movement information processing device further includes
a database constructed in advance by calculating a mean value and a standard deviation of fetal movement amounts for each of the pregnancy weeks based on fetal movement information about fetal movement amounts per unit time for each of the pregnancy weeks collected from many pregnant women in advance, and
a calculator for calculating fetal movement amounts per unit time based on collected fetal movement signals, and
said display/output means graphically displays fetal movement amounts obtained from fetal movement signals collected from the pregnant women along with mean values and standard deviation values obtained from said database.

9. The fetal movement information processing system as claimed in claim 1 wherein said fetal movement information processing device further includes
a database, which is constructed in advance by calculating, based on fetal movement information about fetal movement amounts per unit time collected for each type of fetal movements and for each of pregnancy weeks from many pregnant women in advance, a mean value and a standard deviation of fetal movement amounts for each type of fetal movements and for each of the pregnancy weeks, and
a calculator for calculating fetal movement amounts per unit time based on collected fetal movement signals, and
said display/output means for graphically displaying fetal movement amounts obtained from fetal movement signals collected from the pregnant women along with mean values and standard deviations obtained from said database, for each type of fetal movements.

10. A fetal movement information processing method embodied on a non-transitory computer readable medium and executed by a computer, comprising:
inputting pregnancy information identifying a pregnant woman and information for calculating a number of pregnancy days (STEP-1, STEP-2);
storing fetal movement detection signals detected by a fetal movement sensor in association with detection time information indicating detection times of the fetal movement detection signals in a non-transitory storage device, respectively (STEP-4 to STEP-11);
reading and displaying the stored fetal movement signals in association with detection time information indicating times when the stored fetal movement signals are detected (STEP-12, STEP-13);
calculating fetal movement amounts per unit time based on the read out fetal movement signals (STEP-25); and
displaying and outputting the fetal movement signals or the fetal movement amounts for each of the pregnancy weeks (STEP-30).

11. The fetal movement information processing method as claimed in claim 10 wherein fetal movement detection signals detected by the fetal movement sensor and maternal movement detection signals detected by a maternal movement sensor in association with detection time information indicating detection times of the detection signals, respectively, are stored in said storage device.

12. The fetal movement information processing method as claimed in claim 10 wherein said fetal movement information processing includes classifying the read out fetal movement signals for each type of fetal movements (STEP-19 to STEP-24), and calculating and displaying fetal movement amounts per unit time based on fetal movement information classified for each type of fetal movements (STEP-25 to STEP-27).

13. The fetal movement information processing method as claimed in claim 10 wherein said fetal movement information processing includes rectifying the read out fetal movement signals and integrating the read out fetal movement signals every unit time (STEP-32) and calculating fetal movement amounts per unit time based on fetal movement information including obtained integrated values.

14. The fetal movement information processing method as claimed in claim 10 wherein said fetal movement information processing further includes continuously storing fetal movement signals and maternal movement signals during maternal sleep overnight along with times and displaying waveforms of these signals simultaneously with a time line (STEP-13) in said storage means and designating a time of said time line and enlarging and displaying the waveforms of fetal movement signals and maternal movement signals at the time.

15. The fetal movement information processing method as claimed in claim 10 wherein said fetal movement detected information storing includes deleting fetal movement signals stored in said storage means and measuring fetal movement amounts based on a stop by a switch means or input of event marker which is can be operated by a pregnant woman.

* * * * *